United States Patent
Ibaragi et al.

(10) Patent No.: US 6,660,784 B2
(45) Date of Patent: Dec. 9, 2003

(54) DENTAL CATALYST FOR CHEMICAL POLYMERIZATION AND USE THEREOF

(75) Inventors: Kazuya Ibaragi, Tokuyama (JP); Hideki Kazama, Tokuyama (JP); Makoto Oguri, Tokuyama (JP)

(73) Assignee: Tokuyama Corporation, Yamaguchi (JP)

( * ) Notice: Subject to any disclaimer, the term of this patent is extended or adjusted under 35 U.S.C. 154(b) by 0 days.

(21) Appl. No.: 09/957,025

(22) Filed: Sep. 21, 2001

(65) Prior Publication Data

US 2002/0132951 A1 Sep. 19, 2002

(30) Foreign Application Priority Data

| Sep. 26, 2000 | (JP) | 2000/291528 |
| Oct. 11, 2000 | (JP) | 2000/310992 |
| Oct. 13, 2000 | (JP) | 2000/313519 |

(51) Int. Cl.[7] .................. A61K 6/083; C08K 3/10; C08K 5/55
(52) U.S. Cl. .............. 523/115; 523/116; 523/118; 524/183; 524/184; 524/413
(58) Field of Search ................ 523/115, 116, 523/118; 524/183, 184, 413

(56) References Cited

U.S. PATENT DOCUMENTS

| 5,744,511 A | * | 4/1998 | Kazama et al. | |
| 5,866,631 A | * | 2/1999 | Nakagawa et al. | 523/118 |
| 6,127,451 A | * | 10/2000 | Qian | 523/116 |

* cited by examiner

Primary Examiner—Tae H. Yoon
(74) Attorney, Agent, or Firm—Sherman & Shalloway

(57) ABSTRACT

A dental catalyst for chemical polymerization comprising an acidic compound, an organic peroxide such as cumene hydroperoxide, and aryl borate compound such as sodium tetraphenylborate, but without substantially containing amine compound. This catalyst is chemically highly stable, is easy to handle, is highly active, is less likely to be impaired by polymerization, and does not cause the cured product to be tinted or discolored, and is very useful for the dental restorative.

9 Claims, No Drawings

DENTAL CATALYST FOR CHEMICAL POLYMERIZATION AND USE THEREOF

BACKGROUND OF THE INVENTION

1. Field of the Invention

The present invention relates to a dental catalyst for chemical polymerization used in the field of dental therapy, to a dental adhesive composition using the dental catalyst for chemical polymerization, and to use of the dental curable composition.

2. Description of Prior Arts

A method of curing a polymerizable monomer by using a catalyst for polymerization has been widely employed in the dental field by using, for example, a dental cement, a dental adhesive, a composite resin, a dental self-curing resin, a dental pretreatment material, etc.

These materials require catalysts for polymerization of different kinds depending upon their compositions, objects of use and required properties. The catalysts for polymerization may be divided into those for photo polymerization and those for chemical polymerization. It, however, becomes necessary to use a catalyst for chemical polymerization when the curable composition contains much filler which permits light to pass through little or when the catalyst is used for such applications where it cannot be irradiated with light. Further, the dental adhesive and the pretreatment material, in many cases, require the use of a catalyst for chemical polymerization depending upon the kind of the dental material that is to be adhered. Besides, the catalyst for photo polymerization must be irradiated with light by using a dedicated device. From the standpoint of easy operation, therefore, it is often desired to use the catalyst for chemical polymerization.

In restoring a tooth damaged by, for example, decaying or accident by directly filling the cavity of the tooth with a paste-like dental restorative as represented by a composite resin or a composite polymer followed by curing (direct restoring method), there has been used, as an adhesive (adhesive for directly restoring the teeth), a bonding agent comprising chiefly a polymerizable monomer which contains an acidic group-containing polymerizable monomer. As the bonding agent, there has been developed an excellent material which does not require the pretreatment that was so far needed (Japanese Unexamined Patent Publications (Kokai) Nos. 263604/1997 and 245525/1998). The above bonding agent, however, uses a particular catalyst for photo polymerization, and it has been desired to omit the operation for irradiation with light in order to simplify the adhering operation. Besides, when the above bonding agent is used in combination with a dental restorative of the chemical polymerization type, the unreacted acidic group-containing polymerizable monomer in the bonding agent reacts with an amine component in the organic peroxide/tertiary amine catalyst that is usually used as a catalytic component for chemical polymerization of the dental restorative. As a result, a sufficient degree of adhering strength is not obtained and, hence, the dental restoratives to be used in combination are limited to those of the photo-curable type only, which is a problem.

Further, according to a restoring method (indirect restoring method) by which a dental restorative such as an inlay or a crown prepared in advance outside the oral cavity by using a metal or a ceramic material, is adhered to a tooth, there is used, as an adhesive, a dental adhesive cement such as an adhesive resin cement or a resin-modified glass ionomer cement comprising, chiefly, a polymerizable monomer that contains an acidic group-containing polymerizable monomer and an organic or inorganic filler. These cements, however, often contain fillers in large amounts or are used in combination with metal materials that do not permit light to pass through. It therefore becomes necessary to use a catalyst for chemical polymerization that is capable of executing the polymerization in a dark place at ambient temperature.

A variety of catalysts for chemical polymerization have heretofore been proposed. Examples of the catalyst for chemical polymerization include those of ① a system using a trialkylboran or a partial oxide thereof (Japanese Unexamined Patent Publication (Kokai) No. 108102/1982), ② a redox-type cold self-polymerization initiator such as a system of a combination of an organic peroxide and a cobalt salt or a manganese salt or a system of a combination of an organic peroxide and a tertiary amine (Japanese Unexamined Patent Publication (Kokai) No. 92884/1976), and a system of a combination of hydrogen peroxide and an Fe2+ compound, ③ a system of a barbituric acid, a Cu2+ compound and a Cl–compound (Japanese Unexamined Patent Publication (Kokai) No. 295013/1993), and ④ a system of a combination of an aryl borate compound and an acidic compound (Japanese Unexamined Patent Publication (Kokai) No. 309811/1997) and a system of a combination of an aryl borate compound, an acidic compound and a transition metal compound (Japanese Unexamined Patent Publication (Kokai) No. 227325/1997). Among them, some catalysts have been put into a practical use.

Japanese Unexamined Patent Publication (Kokai) No. 169535/2000 discloses a self-curing resin composition that cures at ambient temperature obtained by blending a composition of a combination of (A) a polymerizable unsaturated compound, (B) a radical-generating catalyst, and a polymerization initiator of an organoboron compound represented by the following general formula (I),

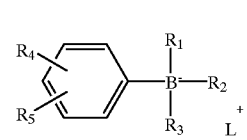

(1)

with an acidic compound or with (A) the acidic polymerizable unsaturated compound. There has been described that this resin composition is effective in the FRP hand-lay-up molding, or in the FRP lining work in the fields of construction and civil engineering.

The system ① which uses the trialkylboran or the partial oxide thereof is an excellent catalyst for chemical polymerization which is very active but is chemically very unstable. Therefore, this catalyst must be packaged separately from other components, must be picked up in suitable amounts just before it is used and must be mixed with other monomer components, requiring cumbersome operation, which is a drawback.

The catalyst ② for chemical polymerization of a combination of the organic peroxide and the tertiary amine and the catalyst ③ for chemical polymerization of the barbituric acid system, are most generally used in the field of dental materials from the standpoint of low beneficial/harmful action to the living bodies and easy availability involving, however, problems as pointed out below.

That is, the catalyst for chemical polymerization of a combination of the organic peroxide and the tertiary amine, involves such problems as tinting the cured product due to oxidation of the amine compound and discoloration, and impairing the polymerization due to oxygen and acidic components (the acidic component here produces a quaternary salt which does not exhibit reducing ability upon reacting with the tertiary amine). The problem of tinting or discoloration causes the color tone to become different from that of a natural tooth when the catalyst is used for a dental restorative as represented by a composite resin, and deteriorates the aesthetic value. The problem of impairing the polymerization means that the catalyst cannot be used for the dental adhesive that uses the acidic group-containing polymerizable monomer as an essential component. The catalyst for chemical polymerization of the barbituric acid type has such problems as difficulty in controlling the curing time and poor preservation stability.

The catalyst ④ for chemical polymerization using the aryl borate is easy to handle, does not cause the cured product to be tinted or discolored, and exhibits excellent preservation stability without, however, exhibiting sufficient activity for polymerization. Therefore, further improved activity has been desired.

SUMMARY OF THE INVENTION

As described above, no dental catalyst for chemical polymerization has yet been known, which is chemically stable, easy to handle, highly active, less subject to be impaired by polymerization, and does not cause the cured product to be tinted or discolored.

It is therefore an object of the present invention to provide a dental catalyst for chemical polymerization having the above excellent features.

In order to accomplish the above-mentioned object, the present inventors have conducted keen study. As a result, the present inventors have discovered that the activity for polymerization is greatly enhanced when an aryl borate compound and an acidic compound are used in combination with a particular oxidizing agent, that the dental curable composition using the above catalyst for chemical polymerization exhibits excellent features as an adhesive, as a pretreatment material or as a restorative, and have completed the present invention.

That is, a first invention is concerned with a dental catalyst for chemical polymerization comprising an aryl borate compound, an acidic compound and an organic peroxide, without substantially containing amine compound which exhibits a catalytic action. The dental catalyst for chemical polymerization of the present invention does not substantially contain amine compound and, hence, does not cause the cured product to be tinted or discolored. Besides, the catalyst is easy to handle, exhibits high activity for polymerization even in the presence of oxygen or an acidic compound, and imparts a suitable degree of surplus operation time. Among the catalysts for dental chemical polymerization of the present invention, the one containing a metal compound for promoting the decomposition of the organic peroxide, exhibits a particularly high polymerizing activity. When the catalyst containing the acidic group-containing polymerizable monomer as an acidic compound, is used as a catalyst for polymerizing the dental curable composition that contains the polymerizable monomer as an essential component, there is no need of adding any other acidic compound, and no acidic compound elutes out from the obtained cured product when it is used.

Though not stuck to the theory, it is considered that in the dental catalyst for chemical polymerization of the present invention, the aryl borate compound is decomposed with the acidic compound to thereby form an aryl borane compound which is then oxidized with oxygen present in the atmosphere to form polymerizable radicals and is further oxidized with an organic peroxide to form more radicals in the curable composition containing less oxygen, to thereby serve as a highly active catalyst for chemical polymerization. Upon containing a metal compound that promotes the decomposition of the organic peroxide, further, oxidation of the aryl borane compound with the organic peroxide is promoted lending the catalyst itself well for use as a more active catalyst for chemical polymerization.

A second invention is concerned with a dental curable composition containing a polymerizable monomer and the dental catalyst for chemical polymerization of the present invention. The dental curable composition of the present invention has a feature in that it undergoes the polymerization at ambient temperature even in a dark place to give an excellently cured product. Further, a dental adhesive composition which further contains a photopolymerization initiator is a curable composition of the so-called dual cure type and has a feature in that it finds a wide range of clinical use.

A third invention is concerned with an adhesive for directly restoring the teeth, comprising a dental curable composition of the present invention containing 100 parts by weight of a polymerizable monomer which contains an acidic group-containing polymerizable monomer, 0.01 to 10 parts by weight of an aryl borate compound, 0.01 to 10 parts by weight an organic peroxide, 1 to 20 parts by weight of a multi valent metal ion-eluting filler and/or 2 to 30 parts by weight of water. The adhesive for directly restoring the teeth (bonding agent) of the present invention strongly adheres to both the dentin and the enamel without the need of pretreating the tooth tissue, can be applied without the need of irradiation with light, and can be used both as the dental restorative of the photo-curing type and the dental restorative of the chemically curing type, which is an excellent feature that could not be found with the existing bonding agents.

Further, a fourth invention is concerned with an adhesive for indirectly restoring the teeth, comprising a dental curable composition of the present invention containing 100 parts by weight of a polymerizable monomer which contains an acidic group-containing polymerizable monomer, 0.01 to 10 parts by weight of an aryl borate compound, 0.01 to 10 parts by weight an organic peroxide, and 50 to 900 parts by weight of a filler.

The adhesive for indirectly restoring the teeth of the present invention has a feature in that it adheres will to both the enamel and the dentin.

A fifth invention is concerned with a dental restorative comprising a dental curable composition of the invention containing a filler in an amount of 50 to 900 parts by weight per 100 parts by weight of the whole polymerizable monomers. The dental restorative is the one that can be used as a material which substitutes for damaged portion of the tooth, and that gives a highly strong cured product without tint or discoloration, making it possible to accomplish a highly aesthetic and highly reliable restoration.

A sixth invention is concerned with a dental pretreatment material comprising a dental curable composition of the present invention which contains an acidic group-containing polymerizable monomer, an aryl borate compound, an organic peroxide and water. Even when the adhesive of the photo polymerization type or the adhesive of the chemical polymerization type is used, the dental pretreatment material of the present invention gives a highly strong adhesiveness to both the enamel and the dentin through one time of application, and maintains a high degree of safety.

DESCRIPTION OF THE PREFERRED EMBODIMENTS

A dental catalyst for chemical polymerization of the present invention comprises an aryl borate compound, an acidic compound and an organic peroxide, but without substantially containing amine compound as a catalyst.

Here, the words "without substantially containing amine compound as a catalyst" means that the catalyst does not contain amine compound in such an amount that neutralizes the acidic compound which is a component in the catalyst for chemical polymerization to substantially impair the function of the catalyst for chemical polymerization. In the polymerizable composition containing a catalyst for chemical polymerization of the present invention, it is allowable that the amine compound is contained in a very small amount (e.g., smaller than 0.1% by weight relative to the acidic compound) for a purpose other than the catalyst for chemical polymerization. When the amine compound is contained as a catalytic component in an amount in excess of the above amount, the initial tint of the cured product increases due to the oxidation of the amine compound and, besides, resistance against being colored decreases arousing a problem from an aesthetic point of view. Besides, the activity for polymerization drops since the acidic compound which is a component of the catalyst for chemical polymerization of the invention is neutralized. Moreover, the amine compound often emits its peculiar offensive odor giving uncomfortable feeling to the patient, which is a problem.

There is no particular limitation on the aryl borate compound used for the catalyst for chemical polymerization of the invention provided it has at least one boron-aryl bond in the molecule. The aryl borate compound used in the invention is represented by the following general formula (1),

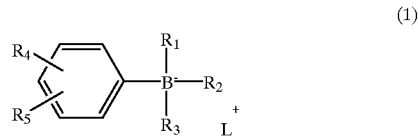

(1)

wherein $R_1$, $R_2$ and $R_3$ are, independently from each other, alkyl groups, aryl groups, aralkyl groups or alkenyl groups which may have a substituent, $R_4$ and $R_5$ are, independently from each other, hydrogen atoms, halogen atoms, alkyl groups which may have a substituent, or phenyl groups which may have a substituent, and $L^+$ is a metallic cation, a quaternary ammonium ion, a quaternary pyridinium ion, a quaternary quinolinium ion or a phosphonium ion.

In the dental clinic, the material that utilizes the curing reaction of the catalyst for chemical polymerization is generally used in a manner that the products separately packaged from the catalyst are mixed or kneaded together just before being used. However, the borate compound without at all having boron-aryl bond has very poor preservation stability and is decomposed upon easily reacting with oxygen in the air. Even in a state of being separately packaged, the borate compound is easily deteriorated, or the curing reaction proceeds during the mixing or kneading, causing the surplus time for operation to be shortened, i.e., making it virtually difficult to use the materials.

Concrete examples of the aryl borate compound represented by the above formula (1) include sodium salt, lithium salt, potassium salt, magnesium salt, tetrabutylammonium salt, tetramethylammonium salt, tetraethylammonium salt, tributylamine salt, triethanolamine salt, methylpyridinium salt, ethylpyridinium salt, butylpyridinium salt, methylquinolinium salt, ethylquinolinium salt and butylquinolinium salt of trialkylphenylboron, trialkyl(p-chlorophenyl)boron, trialkyl(p-fluorophenyl)boron, trialkyl(3,5-bistrifluoromethyl)phenylboron, trialkyl[3,5-bis(1,1,1,3,3,3-hexafluoro-2-methoxy-2-propyl)phenyl]boron, trialkyl(p-nitrophenyl)boron, trialkyl(m-nitrophenyl)boron, trialkyl(p-butylphenyl)boron, trialkyl(m-butylphenyl)boron, trialkyl(p-butyloxyphenyl)boron, trialkyl(m-butyloxyphenyl)boron, trialkyl(p-octyloxyphenyl)boron, and trialkyl(m-octyloxyphenyl)boron (alkyl group is an n-butyl group, an n-octyl group or an n-dodecyl group, etc.) as borate compounds having one aryl group in a molecule.

As the borate compounds having two aryl groups in a molecule, there can be exemplified sodium salt, lithium salt, potassium salt, magnesium salt, tetrabutylammonium salt, tetramethylammonium salt, tetraethylammonium salt, tributylamine salt, triethanolamine salt, methylpyridinium salt, ethylpyridinium salt, butylpyridinium salt, methylquinolinium salt, ethylquinolinium salt and butylquinolinium salt of dialkyldiphenylboron, dialkyldi(p-chlorophenyl)boron, dialkyldi(p-fluorophenyl)boron, dialkyldi(3,5-bistrifluoromethyl)phenylboron, dialkyldi[3,5-bis(1,1,1,3,3,3-hexafluoro-2-methoxy-2-propyl)phenyl]boron, dialkyl(p-nitrophenyl)boron, dialkyldi(m-nitrophenyl)boron, dialkyldi(p-butylphenyl)boron, dialkyldi(m-butylphenyl)boron, dialkyldi(p-butyloxyphenyl)boron, dialkyldi(m-butyloxyphenyl)boron, dialkyldi(p-octyloxyphenyl)boron, and dialkyldi(m-octyloxyphenyl)boron (alkyl group is an n-butyl group, an n-octyl group or an n-dodecyl group, etc.).

As the borate compounds having three aryl groups in a molecule, there can be exemplified sodium salt, lithium salt, potassium salt, magnesium salt, tetrabutylammonium salt, tetramethylammonium salt, tetraethylammonium salt, tributylamine salt, triethanolamine salt, methylpyridinium salt, ethylpyridinium salt, butylpyridinium salt, methylquinolinium salt, ethylquinolinium salt and butylquinolinium salt of monoalkyltriphenylboron, monoalkyltris(p-chlorophenyl)boron, monoalkyltris(p-fluorophenyl)boron, monoalkyltris(3,5-bistrifluoromethyl)phenylboron, monoalkyltris[3,5-bis(1,1,1,3,3,3-hexafluoro-2-methoxy-2-propyl)phenyl]boron, monoalkyltris(p-nitrophenyl)boron, monoalkyltris(m-nitrophenyl)boron, monoalkyltris(p-butylphenyl)boron, monoalkyltris(m-butylphenyl)boron, monoalkyltris(p-butyloxyphenyl)boron, monoalkyltris(m-butyloxyphenyl)boron, monoalkyltris(p-octyloxyphenyl)boron, and monoalkyltris(m-octyloxyphenyl)boron (alkyl group is an n-butyl group, an n-octyl group or an n-dodecyl group, etc.).

As the borate compounds having four aryl groups in a molecule, there can be exemplified sodium salt, lithium salt, potassium salt, magnesium salt, tetrabutylammonium salt, tetramethylammonium salt, tetraethylammonium salt, tributylamine salt, triethanolamine salt, methylpyridinium salt, ethylpyridinium salt, butylpyridinium salt, methylquinolinium salt, ethylquinolinium salt and butylquinolinium salt of tetraphenylboron, tetrakis(p-chlorophenyl)boron, tetrakis(p-fluorophenyl)boron, tetrakis(3,5-bistrifluoromethyl)phenylboron, tetrakis[3,5-bis(1,1,1,3,3,3-hexafluoro-2-methoxy-2-propyl)phenyl]boron, tetrakis(p-nitrophenyl)boron, tetrakis(m-nitrophenyl)boron, tetrakis(p-butylphenyl)boron, tetrakis(m-butylphenyl)boron, tetrakis(p-butyloxyphenyl)boron, tetrakis(m-butyloxyphenyl)boron, tetrakis(p-octyloxyphenyl)boron, and tetrakis(m- octyloxyphenyl)boron (alkyl group is an n-butyl group, an n-octyl group or an n-dodecyl group, etc.).

Among them, it is desired to use a borate compound having three or four aryl groups in a molecule from the standpoint of preservation stability, and it is most desired to use a borate compound having four aryl groups from the standpoint of easy handling and easy availability. These aryl borate compounds may be used in a single kind or being mixed in two or more kind.

As the acidic compound used for the dental catalyst for chemical polymerization of the present invention, there can be used any inorganic acid or organic acid generally known as Brönsted acid without any limitation. Representative examples of the inorganic acid include hydrochloric acid, sulfuric acid, nitric acid and phosphoric acid. Representative examples of the organic acid include carboxylic acids such as acetic acid, propionic acid, maleic acid, fumaric acid, phthalic acid, benzoic acid, trichloroacetic acid, trifluoroacetic acid, citric acid and trimellitic acid; sulfonic acids such as p-toluenesulfonic acid, benzenesulfonic acid, methanesulfonic acid and trifluoromethanesulfonic acid; and phosphoric acids such as methylphosphonic acid, phenylphosphonic acid, dimethylphosphinic acid and diphenylphosphinic acid. There can be further exemplified solid acids such as acidic ion-exchange resin and acidic alumina in addition to phenols and thiols, as preferred acids. As the acidic compound, further, there may be used an acidic group-containing polymerizable monomer containing a polymerizable group. In this case, the acidic compound itself is a polymerizable monomer which is desirable since it will not elute out acidic component upon the curing by polymerization.

As the acidic group-containing polymerizable monomer, there can be used any polymerizable monomer having at least one acidic group and at least one polymerizable unsaturated group in a molecule without any limitation, and a known compound can be used. Here, the acidic group stands for a group that exhibits acidic property in an aqueous solution, such as a phosphinico group {—P(=O)OH}, a phosphono group {—P(=O)(OH)$_2$}, a carboxyl group {—C(=O)OH}, a sulfo group (—SO$_3$H), or an organic group having an acid anhydride skeleton {—C(=O)—O—C(=O)—}. The polymerizable unsaturated group stands for an unsaturated group having a radical polymerization ability, such as a vinyl group, an allyl group, an acryloyl group, a methacryloyl group, an acrylamide group and a methacrylamide group.

As the acidic group-containing polymerizable monomer, there can be preferably used a compound represented by the following general formula (2) or (3), $$(CH_2=\overset{R_6}{\underset{|}{C}}-W)_{\overline{m}}R_7-(X)_n \qquad (2)$$

$$(CH_2=\overset{R_6}{\underset{|}{C}}-W)_{\overline{m}}R_7-\overset{(X)_{n-1}}{\underset{|}{X'}}-\overset{(X)_{n'-1}}{\underset{|}{R'_7}}-(W'-\overset{R_6}{\underset{|}{C}}-CH_2)_n \qquad (3)$$

wherein R$_6$ and R$_6$' are, independently from each other, hydrogen atoms or methyl groups, W and W' are, independently from each other, oxycarbonyl groups (—COO—), iminocarbonyl groups (—CONH—) or phenylene groups (—C$_6$H$_4$—), R$_7$ and R$_7$' are 2- to 6-valent organic residues with 1 to 30 carbon atoms having a bonding hand or an ether bond and/or an ester bond, wherein, when W and W' are oxycarbonyl groups or iminocarbonyl groups, R$_7$ is not a bonding hand, X is a monovalent or divalent acidic group, m and m' are, independently from each other, integers of 1 to 4, m+n is a number of valency of R$_7$, and m'+n' is a number of valency of R$_7$'.

Though there is no particular limitation on their structures provided X and X' in the above general formulas (2) and (3) are acidic groups that comply with the above definitions. concrete examples are as given below.

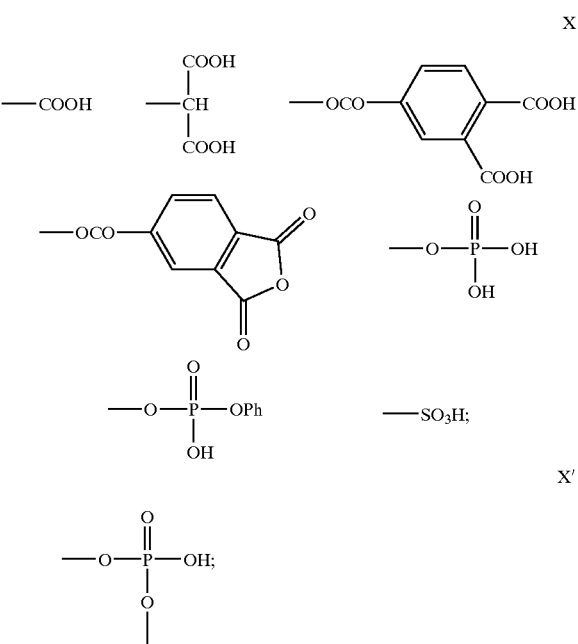

In the above general formulas (2) and (3), there is no particular limitation on the structure of R$_7$, and there may be used a 2- to 6-valent organic residue with 1 to 30 carbon atoms which may have a bonding hand or a known ether bond and/or an ester bond. Concrete examples are as described below. Here, the case where R$_7$ is a bonding hand stands for a state where a group W and a group X are directly bonded to each other. When W is an oxycarbonyl group or an iminocarbonyl group, R$_7$ does not become a bonding hand.

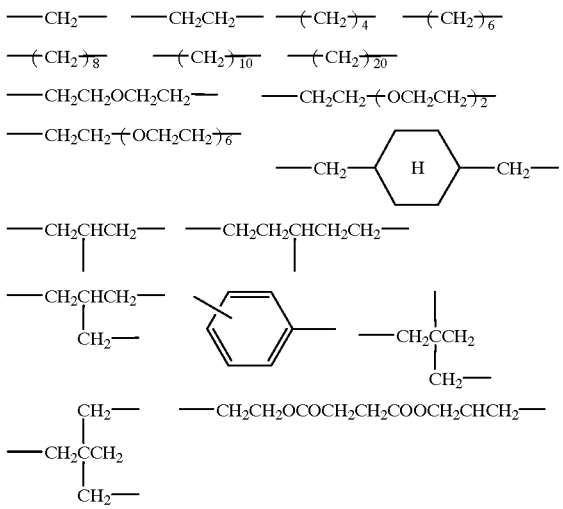

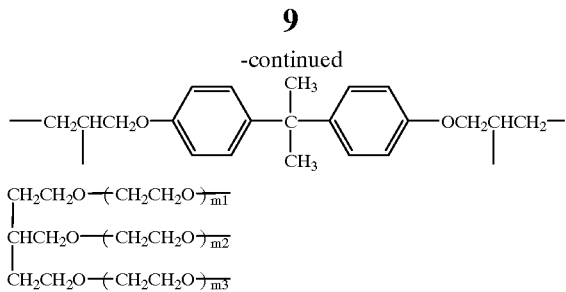

wherein m1, m2 and m3 are, independently from each other, integers of from 0 to 10, and m1+m2+m3 is not smaller than 1.

Preferred examples of the acidic group-containing polymerizable monomers represented by the general formulas (2) and (3) are as follows:

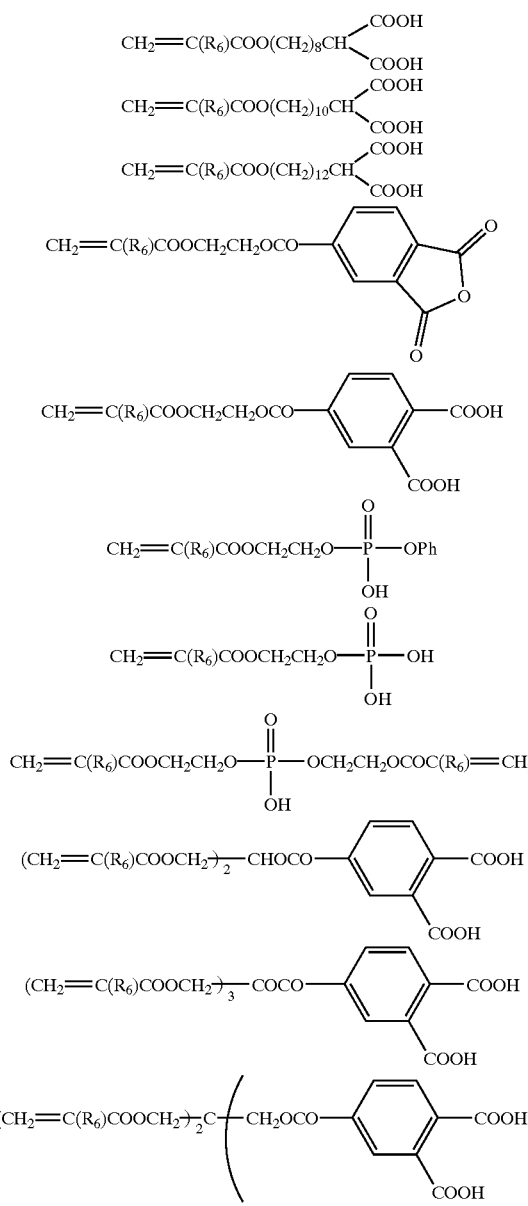

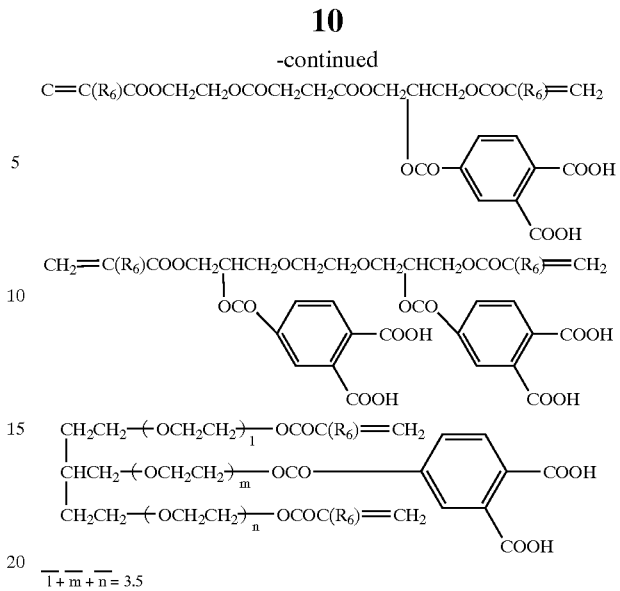

$$\overline{l} + \overline{m} + \overline{n} = 3.5$$

wherein l, m and n are, independently from each other, integers of 0 to 2. In the formulas, the compounds of the lowest stages have l, m and n which are not the same, and the sum of l, m and n in the mixture thereof is 3.5 in average.

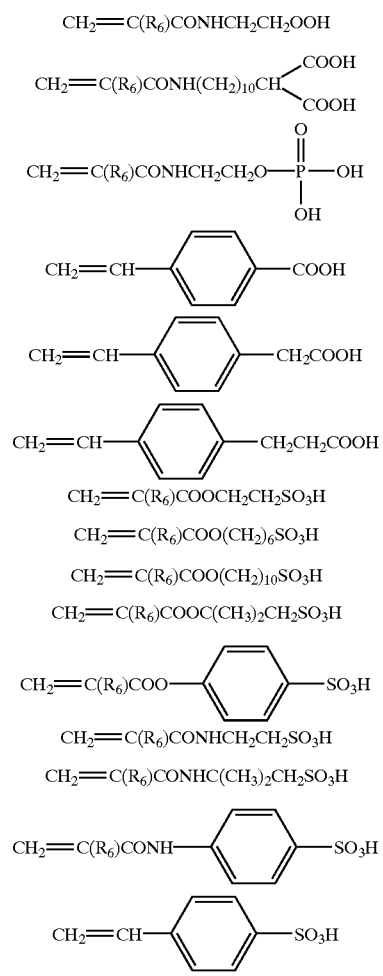

-continued

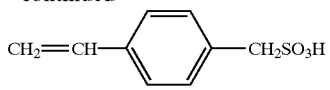

wherein $R_6$ is a hydrogen atom or a methyl group. Vinylphosphonic acids, acrylic acid, methacrylic acid and vinylsulfonic acids are included in the acidic group-containing polymerizable monomers.

The acidic group-containing polymerizable monomers can be used alone or being mixed together in two or more kinds.

Among the acidic group-containing polymerizable monomers concretely described above, it is particularly preferred to use those having a phosphinico group {=P(=O)OH}, a phosphono group {—P(=O)(OH)$_2$} or a carboxyl group {—C(=O)OH} as an acidic group.

There is no particular limitation on the amount of the acidic compound used for the dental catalyst for chemical polymerization of the present invention. From the standpoint of activity for polymerization and curing property, however, it is desired to use the acidic compound in an amount of from 0.1 to 100 mol equivalent and, particularly, in an amount of from 0.5 to 50 mol equivalent per a mole equivalent of the aryl borate compound.

The dental catalyst for chemical polymerization of the present invention contains an organic peroxide as an oxidizing agent. As the organic peroxide, any known compound can be used without limitation.

As a representative organic peroxide that can be used in the present invention, there can be exemplified a variety of organic peroxides that can be grouped into ketone peroxides, peroxy ketals, hydroperoxides, dialkyl peroxides, peroxy esters, diacyl peroxides, and peroxy dicarbonates. Described below are concrete examples of these organic peroxides.

As the ketone peroxides, there can be exemplified methyl ethyl ketone peroxide, cyclohexanone peroxide, methylcyclohexanone peroxide, methylacetoacetate peroxide and acetylacetone peroxide.

As the peroxy ketals, there can be exemplified 1,1-bis(t-hexylperoxy)-3,3,5-trimethylcyclohexane, 1,1-bis(t-hexylperoxy)cyclohexane, 1,1-bis(t-butylperoxy)-3,3,5-trimethylcyclohexane, 1,1-bis(t-butylperoxy)cyclohexane, 1,1-bis(t-butylperoxy)cyclododecane, 2,2-bis(t-butylperoxy)butane, n-butyl-4,4-bis(t-butylperoxy)valerate, 2,2-bis(4,4-di-t-butylperoxycyclohexyl)propane.

As the hydroperoxides, there can be exemplified p-menthane hydroperoxide, diisopropylbenzene hydroperoxide, 1,1,3,3-tetramethylbutyl hydroperoxide, cumene hydroperoxide, t-hexyl hydroperoxide, t-butyl hydroperoxide, etc.

As the dialkyl peroxide, there can be exemplified α,α-bis(t-butylperoxy)diisopropylbenzene, dicumyl peroxide, 2,5-dimethyl-2,5-bis(t-butylperoxy)hexane, t-butylcumyl peroxide, di-t-butyl peroxide, 2,5-dimethyl-2,5-bis(t-butylperoxy)hexyne-3, etc.

As the diacyl peroxides, there can be exemplified isobutyryl peroxide, 2,4-dichlorobenzoyl peroxide, 3,5,5-trimethylhexanoyl peroxide, octanoyl peroxide, lauroyl peroxide, stearyl peroxide, succinic acid peroxide, m-toluoylbenzoyl peroxide and benzoyl peroxide.

As the peroxycarbonates, there can be exemplified di-n-propyl peroxydicarbonate, diisopropyl peroxydicarbonate, bis(4-t-butylcyclohexyl) peroxydicarbonate, di-2-ethoxyethyl peroxydicarbonate, di-2-ethylhexyl peroxydicarbonate, di-2-methoxybutyl peroxydicarbonate and di(3-methyl-3-methoxybutyl) peroxydicarbonate.

As the peroxy esters, there can be exemplified α,α-bis(neodecanoyl peroxy)diisopropylbenzene, cumyl peroxy neodecanoate, 1,1,3,3-tetramethylbutyl peroxyneodecanoate, 1-cyclohexyl-1-methylethyl peroxyneodecanoate, t-hexyl peroxyneodecanoate, t-butyl peroxyneodecanoate, t-hexyl peroxypivarate, t-butyl peroxypivarate, 1,1,3,3-tetramethylbutyl peroxy-2-ethylhexanoate, 2,5-dimethyl-2,5-bis(2-ethylhexanoyl peroxy)hexane, 1-cyclohexyl-1-methylethyl peroxy-2-ethylhexanoate, t-hexyl peroxy-2-ethylhexanoate, t-butyl peroxy-2-ethylhexanoate, t-butyl peroxyisobutylate, t-hexyl peroxyisopropyl monocarbonate, t-butyl peroxymaleic acid, t-butyl peroxy-3,5,5-trimethylhexanoate, t-butyl peroxylaurate, 2,5-dimethyl-2,5-bis(m-toluoyl peroxy) hexane, t-butyl peroxyisopropyl monocarbonate, t-butyl peroxy-2-ethylhexyl monocarbonate, t-hexyl peroxy benzoate, 2,5-dimethyl-2,5-bis(benzoyl peroxy)hexane, t-butyl peroxyacetate, t-butyl peroxy-m-toluoyl benzoate, t-butyl peroxybenzoate and bis(t-butyl peroxy)isophthalate.

In addition to the above, there can be preferably used t-butyltrimethylsilyl proxide and 3,3', 4,4'-tetra(t-butyl peroxycarbonyl)benzophenone, etc.

These organic peroxides may be used being suitably selected depending upon the kinds and amounts of the aryl borate compound and the acidic compound that are used in combination, and may be used in a single kind or being mixed in two or more kinds. From the standpoint of activity for polymerization, however, it is desired to use hydroperoxides, ketone peroxides, peroxy esters or diacyl peroxides. Among them, it is desired to use an organic peroxide having a 10-hour half-life temperature of not lower than 60° C. from the standpoint of preservation stability when it is used as the curable composition.

There is no particular limitation on the amount of the organic peroxide used for the dental catalyst for chemical polymerization of the present invention. From the standpoint of activity for polymerization, however, it is desired to use the organic peroxide in an amount of from 0.1 to 10 mole equivalent and, particularly, from 0.5 to 5 mole equivalent per a mole equivalent of the aryl borate compound. In order to further improve the activity for polymerization of the dental catalyst for chemical polymerization of the present invention, it is desired to add a metal compound (hereinafter also simply referred to as decomposition promoting agent) which promotes the decomposition of the organic peroxide that is used. When an amine compound is added, even a compound having an action for decomposing the organic peroxide neutralizes the acidic compound which is one of the catalytic components to deteriorate the activity for polymerization.

Any decomposition promoting agent can be used in the present invention provided it is a metal compound having action for promoting the decomposition of the organic peroxide when it is present together with the aryl borate compound. Concrete examples of the decomposition promoting agent having such an action include iron compounds such as iron chloride (III), iron (III) acetylacetonato, iron naphthenate (III), and iron citrate (III); copper compounds such as copper chloride (II), copper citrate (II), copper (II) acetylacetonato and copper (II) stearate; molybdenum compounds such as molybdenum oxide (VI), and molybdenum oxide acetylacetonato; manganese compounds such as manganese oxide (IV) and manganese naphthenate; cobalt compounds such as cobalt naphthenate and cobalt (III) acetylacetonato; tungsten compounds such as tungsten oxide (VI), sodium tungstate and silicotungstic acid; tin compounds such as dibutyltin oxide (IV); and metal alkoxides such as titanium tetrabutoxide and aluminum tributoxide. Though there is no particular limitation on the amount of use, it is desired that the decomposition promoting agent is used in an amount of from 0.001 to 1 mole equivalent and, particularly, from 0.05 to 0.1 mole equivalent per mole equivalent of the organic peroxide from the standpoint of activity for polymerization.

The dental catalyst for chemical polymerization of the present invention does not substantially contain amine compound and, hence, does not cause the cured product to be tinted or discolored, is easy to handle, is highly active for polymerization, and makes it possible to maintain a suitable degree of surplus operation time and can, hence, be suitably used as a catalyst for polymerizing dental curable compositions that contain various polymerizable monomers. Here, any known polymerizable monomer can be used without limitation in combination with a dental catalyst for chemical polymerization that has heretofore been used in the dental field. From the standpoint of curing rate, however, it is desired to use a (meth)acrylate monomer.

Concrete examples of the (meth)acrylate polymerizable monomer that can be preferably used include mono(meth)acrylate monomers such as methyl (meth)acrylate, ethyl (meth)acrylate, butyl (meth)acrylate, glycidyl (meth)acrylate, 2-cyanomethyl (meth)acrylate, benzyl methacrylate, polyethylene glycol mono(meth)acrylate, allyl (meth)acrylate, 2-hydroxyethyl (meth)acrylate, 3-hydroxypropyl (meth)acrylate, and glyceryl mono(meth)acrylate; and polyfunctional (meth)acrylate monomers such as ethylene glycol di(meth)acrylate, diethylene glycol di(meth)acrylate, triethylene glycol di(meth)acrylate, nonaethylene glycol di(meth)acrylate, propylene glycol di(meth)acrylate, dipropylene glycol di(meth)acrylate, 2,2'-bis[4-(meth)acryloyloxyethoxyphenyl]propane, 2,2'-bis[4-(meth)acryloyloxyethoxyethoxyphenyl]propane, 2,2'-bis{4-[3-(meth)acryloyloxy-2-hydroxypropoxy]phenyl}propane, 1,4-butanediol di(meth)acrylate, 1,6-hexanediol di(meth)acrylate, 1,9-nonanediol di(meth)acrylate, trimethylolpropane tri(meth)acrylate, neopentylglycol di(meth)acrylate, urethane (meth)acrylate, and epoxy (meth)acrylate. These (meth)acrylate monomers can be used alone or being mixed in two or more kinds.

The dental curable composition of the present invention can be polymerized being mixed with other polymerizable monomers for adjusting the viscosity of the curable composition or for adjusting other properties in addition to being mixed with the above-mentioned (meth)acrylate monomers. It is here desired that the blending ratio of the (meth)acrylate monomers is not smaller than 50% by weight and, preferably, not smaller than 60% by weight per the whole polymerizable monomers. When the blending ratio is smaller than 50% by weight, it becomes difficult to obtain a required curing rate in the dental clinic.

Examples of other polymerizable monomers that can be used in the invention include styrene or α-methylstyrene derivatives such as styrene, p-chlorostyrene, p-hydroxystyrene, divinylbenzene and α-methylstyrene; fumaric acid ester compounds such as monomethyl fumarate, diethyl fumarate and diphenyl fumarate; allyl compounds such as diallyl phthalate, diallyl terephthalate, diallyl carbonate and allyl diglycol carbonate; epoxy compounds such as diglycerol polyglycidyl ether, pentaerythritol polyglycidyl ether, 1,4-bis(2,3-epoxypropoxyperfluoroisopropyl)cyclohexane, sorbitol polyglycidyl ether, trimethylolpropane polyglycidyl ether, resorcine diglycidyl ether, 1,6-hexanediol diglycidyl ether, polyethylene glycol diglycidyl ether, phenyl glycidyl ether, p-tert-butylphenyl glycidyl ether, adipic acid diglycidyl ether, o-phthalic acid diglycidyl ether, dibromophenyl glycidyl ether, 1,2,7,8-diepoxyoctane, 4,4,'-bis(2,3-epoxypropoxyperfluoroisopropyl) diphenyl ether, 3,4-epoxycyclohexylmethyl-3',4'-epoxycyclohexane carboxylate, 3,4-epoxycyclohexyloxysilane, and ethylene glycol-bis(3,4-epoxycyclohexane carboxylate); oxetane compounds such as 3-ethyl-3-hydroxymethyloxetane, 3-ethyl-3-(phenoxymethyl)oxetane, 3-ethyl-3-(naphthoxymethyl)oxetane, di[1-ethyl(3-oxetanyl)]methyl ether, 3-ethyl-3-(2-ethylhexyloxymethyl)oxetane, and 1,4-bis{[(3-ethyl-3-oxetanyl)methoxy]methyl}benzene; and vinyl ether compounds such as vinyl 2-chloroethyl ether, vinyl n-butyl ether, triethylene glycol divinyl ether, 1,4-cyclohexanedimethanol divinyl ether, trimethylolethane trivinyl ether, and vinyl glycidyl ether. Among the above other polymerizable monomers, the epoxy compound, oxetane compound and vinyl ether compounds are cationically polymerizable monomers that start the polymerization with the acidic compound which is one of the components of the dental catalyst for chemical polymerization of the present invention. The above other polymerizable monomers may be used in one kind or in two or more kinds being mixed together.

There is no particular limitation on the ratio of the amount of the polymerizable monomer and the amount of the dental catalyst for chemical polymerization in the curable composition of the invention provided the ratio is sufficient for curing the polymerizable monomer. Generally, however, it is desired that the dental catalyst for chemical polymerization of the invention is used at a ratio of from 0.01 to 20 parts by weight and, particularly, from 0.1 to 10 parts by weight per 100 parts by weight of the whole polymerizable monomers.

The dental curable composition containing the polymerizable monomer and the catalyst for dental polymerization of the invention, may further contain other catalyst for chemical polymerization (catalyst for heat polymerization) and catalyst for photopolymerization using ultraviolet rays or visible rays (hereinafter also referred to simply as other catalysts for polymerization) in addition to the dental catalyst for chemical polymerization of the invention. When the catalyst for photopolymerization is also used, there can be obtained a curable composition of the so-called dual cure-type capable of being cured either chemically or optically.

There is no limitation on the other catalysts for polymerization that are also used. Preferably, however, there can be used azo compounds such as azobisisobutylonitrile and the like as a catalyst for heat polymerization.

As the catalyst for polymerization by ultraviolet rays or visible rays, there can be preferably used α-diketones such as diacetyl, acetyl benzoyl, benzil, 2,3-pentanedion, 2,3-octanedion, 4,4,-dimethoxybenzil, 4,4,-oxybenzil, camphorquinone, 9,10-phenanthrenequinone and acenaphthenequinone; benzoinealkyl ethers such as benzoin methyl ether, benzoin ethyl ether, and benzoin propyl ether; thioxanthone derivatives such as 2,4-diethoxythioxanthone, 2-chlorothioxanthone and methylthioxanthone; benzophenone derivatives such as benzophenone, p,p'-dimethylaminobenzophenone, and p,p'-methoxybenzophenone; acylphosphine oxide derivatives such as 2,4,6-trimethylbenzoyldiphenylphosphine oxide, bis(2,6-dimethoxybenzoyl)-2,4,4-trimethylpentylphosphine oxide, and bis(2,4,6-trimethylbenzoyl)phenylphosphine oxide, as well as a system of a combination of an aryl borate compound which is an essential component of the present invention, a photo sensitized dye and a photo acid generator, i.e., a system comprising an aryl borate/aphoto sensitized dye/a photo acid generating agent. Among them, it is particularly desired to use a system of a combination of an α-diketone and acylphosphine oxide photopolymerization initiator, a photo sensitized dye and a photo acid generator. In this case, it is allowed to prepare a curable composition of the so-called dual curing-type which can be cured either chemically or optically.

As the α-diketone, there can be preferably used camphorquinone and benzil. As the acylphosphone oxide, there can be preferably used 2,4,6-trimethylbenzoyldiphenylphosphone oxide, bis(2,6-dimethoxybenzoyl)-2,4,4-trimethylpentylphosphine oxide, and bis(2,4,6-trimethylbenzoyl)phenylphosphine oxide.

As the photo sensitized dye used for the photopolymerization initiator of the aryl borate/photo sensitized dye/photo acid generator, there can be exemplified a photo sensitized dye of the cumarin type. Particularly preferred cumarin photo sensitized dye has a maximum absorption wavelength in the visible ray region of 400 to 500 nm to exhibit high sensitivity to the irradiation device which is generally used for the dental applications. Representative examples of the cumarin photo sensitized dye include 3-thienoylcumarin, 3,3'-carbonylbis(7-diethylamino)cumarin, 3,3'-carbonylbis(4-cyano-7-diethylaminocumarin, and the like.

The above-mentioned photo acid generator is the one that generates Bronsted acid or Lewis acid, and any known agent can be used without limitation provided it undergoes the decomposition with the photo sensitized dye under the irradiation of visible rays to generate the acid. As the photo acid generator, there is particularly preferably used a halomethyl group-substituted-s-triazine derivative or a diphenyl iodonium salt compound since it generates the acid highly efficiently under the irradiation with visible light rays.

Representative examples of the halomethyl group-substituted-s-triazine derivative include 2,4,6-tris(trichloromethyl)-s-triazine, 2-methyl-4,6-bis(trichloromethyl)-s-triazine, and 2-(2,4-dichlorophenyl)-4,6-bis(trichloromethyl)-s-triazine.

Further, preferred examples of the diphenyl iodonium salt compound include bromides, tetrafluoroborate, hexafluorophosphate, hexafluoroantimonate and trifluoromethanesulfonate of diphenyl iodonium, p-octyloxyphenylphenyl iodonium, and the like.

The above-mentioned other catalysts for polymerization are used not only in a single kind but also in plural kinds in combination, as required. There is no particular limitation on the amount of the other catalysts for polymerization provided it does not impair the effect of the invention. Preferably, however, the other catalysts for polymerization are used in an amount of from 1 to 1000 parts by weight and, particularly, from 10 to 500 parts by weight per 100 parts by weight of the dental catalyst for chemical polymerization of the invention.

The curable composition of the present invention may be further added with a variety of fillers, organic solvent, water, viscosity-imparting agent, ultraviolet ray-absorber, polymerization adjusting agent, dye, antistatic agent, pigment and perfume in order to impart physical properties required for the use. When the curable composition is to be used, for example, as a dental adhesive such as an adhesive for directly restoring the teeth (bonding agent) or as an adhesive for indirectly restoring the teeth, or is used as a dental restorative like a composite resin, it is desired that the curable composition is blended with a filler such as an inorganic filler, an organic filler, or an organic/inorganic composite filler. When the curable composition is to be used as a dental pretreatment material such as a primer, it is desired to add water or an organic solvent thereto. Further, when the curable composition is to be used as a surface lustering material, or is used for restoring a denture, or for preparing a temporarily used crown or bridge, it is desired to add a variety of additives that have generally been used for the materials of this kind.

The curable composition of the present invention is finally used by mixing all of the components together. Here, in order to prevent the deterioration during the preservation, the curable composition, as required, may be packaged in two stable packages. A general combination consists of a package (A) containing some of the polymerizable monomer, the organic peroxide and the acidic compound, and a package (B) containing the remainder of the polymerizable monomer and the aryl borate compound.

The dental curable composition of the present invention can be used for a variety of dental materials, and exhibits excellent features that could not be obtained from the conventional products when it is used as an adhesive for directly restoring the teeth, as an adhesive for indirectly restoring the teeth, as a dental restorative and as a dental pretreatment material.

The adhesive for directly restoring the teeth (bonding agent) of the present invention comprising the dental curable composition of the invention containing 100 parts by weight of a polymerizable monomer containing an acidic group-containing polymerizable monomer, 0.01 to 10 parts by weight of the aryl borate compound, 0.01 to 10 parts by weight of the organic peroxide, and 1 to 20 arts by weight of a multi-valent metal ion-eluting filler and/or 2 to 30 parts by weight of water, imparts a large adhering strength to both the dentin and the enamel even without effecting the pretreatment for the dentin, can be applied without the need of irradiation with light, and can be used as the dental restorative of either the photo curing type or the chemically curing type, which are the features that could not be obtained with the conventional bonding agents. Here, the adhesive for directly restoring the teeth stands for an adhesive (bonding agent) that is used for the method of direct restoration as represented by the adhesion to the composite resin and to the dentin.

Further, the adhesive for indirectly restoring the teeth of the present invention comprising the dental curable composition of the invention containing 100 parts by weight of a polymerizable monomer containing an acidic group-containing polymerizable monomer, 0.01 to 10 parts by weight of the aryl borate compound, 0.01 to 10 parts by weight of the organic peroxide, and 50 to 900 arts by weight of a filler, exhibits a feature of strong adhesiveness to both the enamel and the dentin. Here, the adhesive for indirectly restoring the teeth stands for an adhesive such as an adhesive resin cement or a resin-modified glass ionomer cement that is used for the method of indirect restoration as represented by the adhesion to the crown and to the tooth tissue.

Further, the dental restorative of the present invention comprising the dental curable composition of the invention containing 50 to 900 parts by weight of the filler per 100 parts by weight of the whole polymerizable monomers, is capable of providing a highly strong cured product without tint or discoloration and makes it possible to restore the teeth aesthetically maintaining a high degree of reliability.

Further, the dental pretreatment material of the invention comprising the dental curable composition of the invention containing the acidic group-containing polymerizable monomer, the aryl borate compound, the organic peroxide, and water, gives a large adhering strength to both the enamel and the dentin through one time of application either when the photo polymerizable adhesive or the chemically polymerizable adhesive is used, maintaining a high degree of safety.

These materials will now be described in detail. (I) The adhesive for directly restoring the teeth of the invention and the adhesive for indirectly restoring the teeth of the invention (hereinafter also referred to as adhesives of the invention).

The acidic group-containing polymerizable monomer used for the adhesives of the present invention also works as an acidic compound in the dental catalyst for chemical polymerization of the present invention. As the acidic group-containing polymerizable monomer, there can be used those described above as the acidic compounds without limitation. From the standpoint of adhering strength to the dentin or to the base metal, however, the compounds represented by the above-mentioned general formula (2) or (3) are preferably used.

Among them, a phosphoric acid group (phosphinico group or phosphono group)-containing polymerizable monomer makes it possible to realize a larger adhering strength. Moreover, use of the phosphoric acid group-containing polymerizable monomer and the carboxyl group-containing polymerizable monomer in combination, makes it possible to realize a larger adhering strength to the dentin with less dispersion in the adhering strength. The ratio of blending the phosphoric acid group-containing polymerizable monomer and the carboxyl group-containing polymerizable monomer may be arbitrarily determined depending upon the kinds and amounts of other components that will be used in combination. Preferred examples of the combination of the phosphoric acid group-containing polymerizable monomer and the carboxyl group-containing polymerizable monomer will be a combination of a 2-(meth)acryloyloxyethyldihydrogen phosphate and an 11-methacryloyloxy-1,1-undecanedicarboxylic acid; a combination of a 2-(meth)acryloyloxyethyldihydrogen phosphate and a 4-(meth)acryloyloxyethyltrimellitic anhydride; and a combination of a 10-(meth)acryloyloxydecyl acid phosphate and an 11-methacryloyloxy-1,1-undecanedicarboxylic acid.

The polymerizable monomer used for the adhesives of the present invention may comprise the above-mentioned acidic group-containing polymerizable monomer only but desirably contains a polymerizable monomer without acidic group as well, from the standpoint of the strength of the cured product and the durability of adhesion. Desirably, however, the content of the acidic group-containing polymerizable monomer in the whole polymerizable monomers is from 5 to 70% by weight and, particularly, from 10 to 50% by weight from the standpoint of adhering strength.

The polymerizable monomer without acidic group has at least one polymerizable unsaturated group in a molecule, and may be any one of the polymerizable monomers that were described above to be usable for the dental curable composition of the invention without limitation provided it is the polymerizable monomer other than the above-mentioned acidic group-containing polymerizable monomers. As the polymerizable unsaturated group of the polymerizable monomer, there can be exemplified those similar to the above-mentioned acidic group-containing polymerizable monomers. From the standpoint of curing rate, however, it is desired to use acryloyl group, methacryloyl group, acrylamide group or methacrylamide group.

The dental adhesive of the present invention may further contain, as other polymerizable monomers, a polymerizable monomer having a functional group that bonds to a noble metal so as to adhere to the noble metal material for restoring the crown. Preferred examples of the polymerizable monomer include polymerizable monomers having functional groups such as thiouracil derivative, triazinedithion derivative and mercaptothiazole derivative. As these polymerizable monomers, there can be used a variety of polymerizable monomers represented by the following general formulas.

That is, polymerizable monomers capable of forming mercapto groups by tautomerism represented by the following general formulas (4) to (8); polymerizable monomers having a disulfide group represented by the following general formulas (9) to (12); and polymerizable monomers having a chain-like or cyclic thioether group represented by the following general formulas (13) to (14),

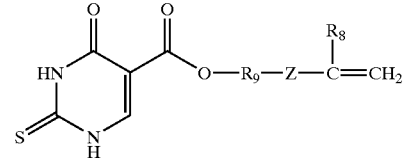

(4)

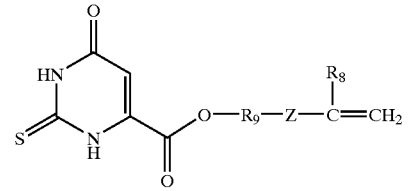

(5)

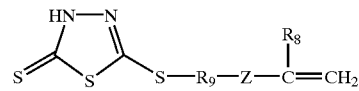

(6)

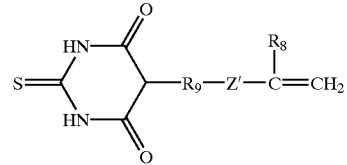

(7)

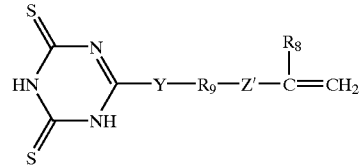

(8)

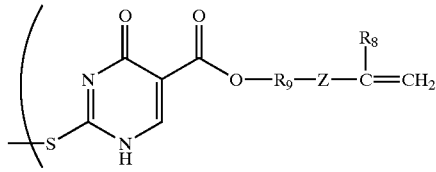

(9)

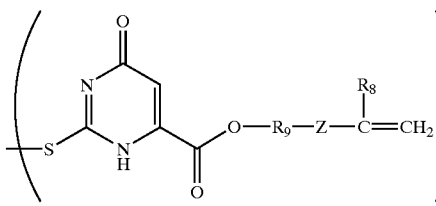

(10)

-continued

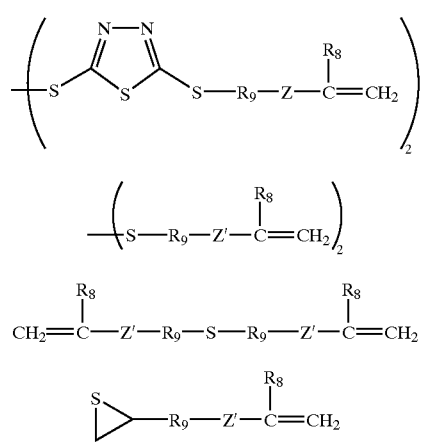

wherein R$_8$ is a hydrogen atom or a methyl group, R$_9$ is a saturated hydrocarbon group having 1 to 12 carbon atoms, a group —CH$_2$—C$_6$H$_4$—CH$_2$—, a group —(CH$_2$)$_o$—Si(CH$_3$)$_2$OSi(CH$_3$)$_2$—(CH$_2$)$_p$— (o and p are, independently from each other, integers of 1 to 5) or a group —CH$_2$CH$_2$OCH$_2$CH$_2$—, Z is a group —OCO—, a group —OCH$_2$— or a group —OCH$_2$—C$_6$H$_4$— (in each group, a carbon atom at the right end is bonded to the unsaturated carbon atom, and an oxygen atom at the left end is bonded to the group R$_4$), Z' is a group —OCO—, a group —C$_6$H$_4$— or a bonding hand (in the case of the group —OCO—, a carbon atom at the right end is bonded to the unsaturated carbon atom, and an oxygen atom at the left end is bonded to the group R$_4$), and Y is —S—, —O— or —N(R')— (R' is a hydrogen atom or an alkyl group having 1 to 5 carbon atoms, and wherein the case where the group Z' is a bonding hand stands for a state where the group Rg and the unsaturated carbon atom are directly bonded together.

Concrete examples of these compounds are the following polymerizable monomers capable of forming a mercapto group by tautomerism represented by the above general formulas (4) to (8),

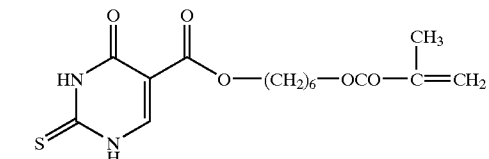

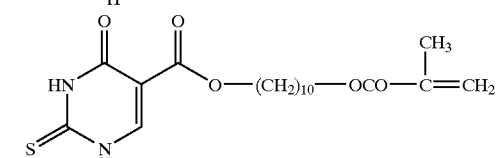

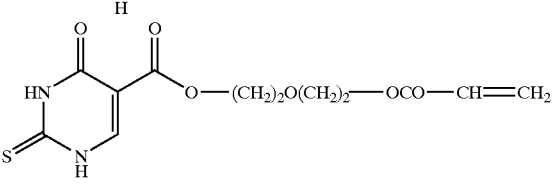

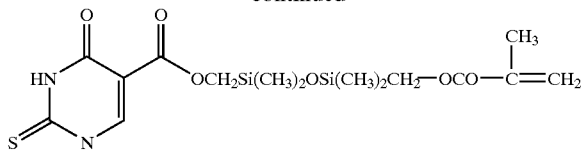

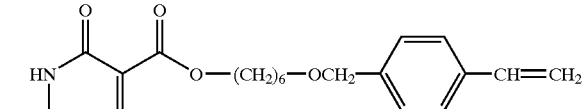

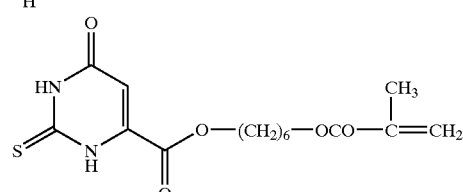

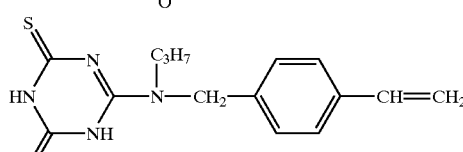

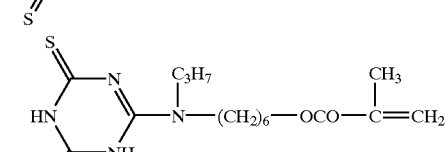

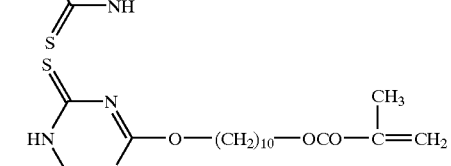

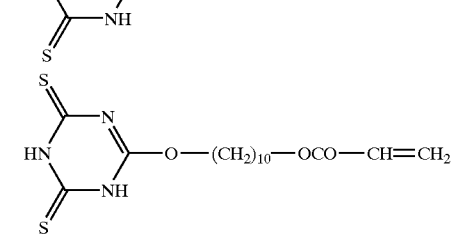

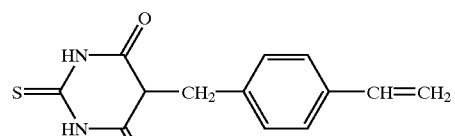

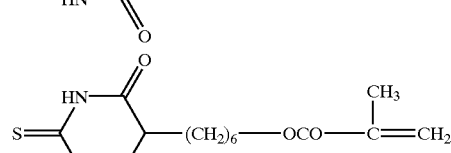

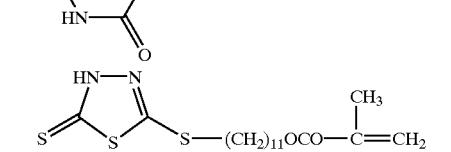

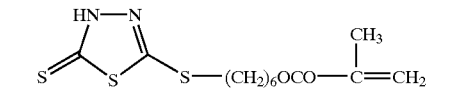

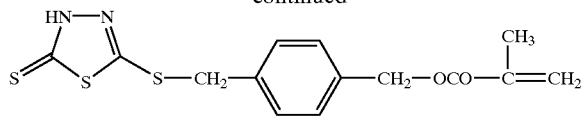

As the polymerizable monomers having the disulfide group represented by the above general formulas (9) to (12), there can be exemplified the following compounds,

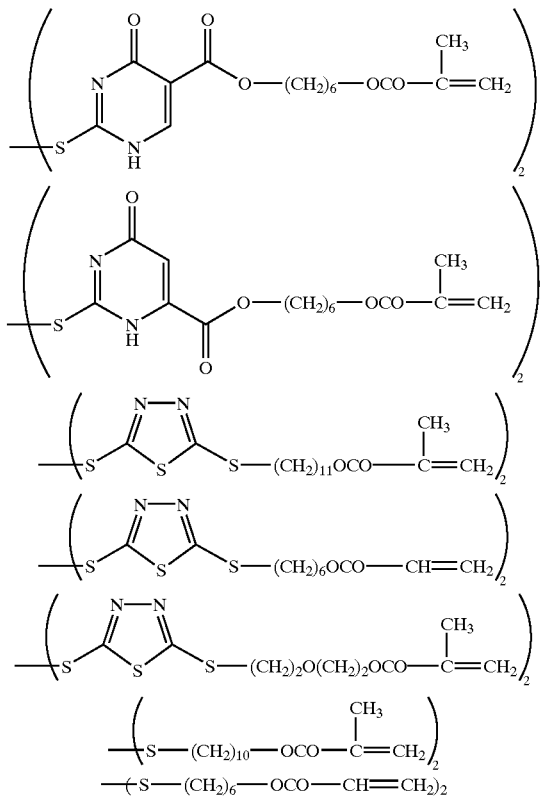

As the polymerizable monomers having a chain-like or cyclic thioether group represented by the above general formulas (13) to (14), there can be exemplified the following compounds,

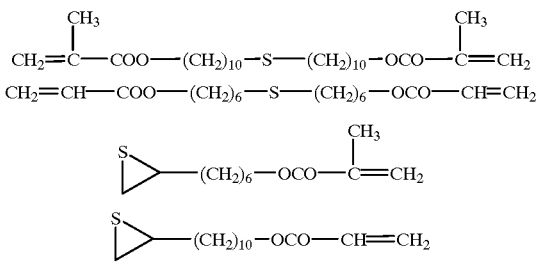

The polymerizable monomers having a functional group that bonds to these noble metals can be used alone or in a mixture of two or more kinds. The blending amount may be suitably determined by taking the viscosity of the composition and the mechanical strength of the cured product into consideration. Generally, however, the polymerizable monomer is used in an amount of from 0.1 to 50 parts by weight and, more preferably, from 0.2 to 20 parts by weight per 100 parts by weight of the whole polymerizable monomers in the dental adhesive.

The aryl borate compound used for the adhesives of the present invention is one of the components of the dental catalyst for chemical polymerization of the invention, and those described above can be used without limitation. To obtain an excellent effect of adhesion, the aryl borate compound must be used in an amount of from 0.01 to 10% by weight with respect to the whole polymerizable monomers. Though the optimum amount of use may differ depending upon the kind and amount of the polymerizable monomer that is used and upon the ratio of blending other components, it is usually desired that the aryl borate compound is used in an amount of from 0.05 to 8% by weight and, particularly, from 0.5 to 6% by weight.

The organic peroxide used for the adhesive of the present invention is one of the components of the dental catalyst for chemical polymerization of the invention, and those described above can be used without any limitation. To obtain an excellent effect of adhesion, the organic peroxide must be used in an amount of from 0.01 to 10% by weight with respect to the whole polymerizable monomers. Though the optimum amount of use may differ depending upon the kind and amount of the polymerizable monomer that is used and upon the ratio of blending other components, it is usually desired that the organic peroxide is used in an amount of from 0.05 to 8% by weight and, particularly, from 0.5 to 5% by weight.

In order to further enhance the adhering property of the adhesive of the invention, it is desired to further add the decomposition promoting agent described earlier.

When the adhesive of the invention is the one for directly restoring the teeth (bonding agent), it is desired that a multi-valent metal ion-eluting filler is added as the filler. By adding this filler, the chelate reaction proceeds between the acidic group-containing polymerizable monomer and the multi-valent metal ions accompanying the polymerization reaction, making it possible to increase the strength of the cured product. There is no particular limitation on the multi-valent metal ion-eluting filler provided it has properties as described above. Concrete examples of the multi-valent metal ion-eluting filler that can be used in the invention include hydroxides such as calcium hydroxide and strontium hydroxide, as well as zinc oxide, silicate glass, fluoroaluminosilicate glass, barium glass and strontium glass. Among them, the fluoroaluminosilicate glass exhibits the most excellent properties in regard to tint resistance of the cured product, and is preferably used. The fluoroaluminosilicate glass may be the known one that is used as a dental cement. A widely known fluoroaluminosilicate glass has a composition comprising, as ionic percent by weight, 10 to 33 of silicon, 4 to 30 of aluminum, 5 to 36 of an alkaline earth metal, 0 to 10 of an alkali metal, 0.2 to 16 of phosphorus, 2 to 40 of fluorine, and the remainder of oxygen. In addition to the one of the above composition, there can be further used the one in which part or whole of the alkaline earth metals are replaced by magnesium, strontium or barium. In particular, the filler substituted by strontium provides the cured product with X-ray nonpermeating property and with a large strength, and is often favorably used. The multi-valent metal ion-eluting filler may be treated with a surface-treating agent as represented by a silane coupling agent. The surfaces may be treated by a known method, and the silane coupling agent is preferably a γ-methacryloxypropyltrimethoxysilane, an ε-methacryloxyoctyltrimethoxysilane or a vinyltrimethoxysilane.

The multi-valent metal ion-eluting filler may be added in an amount of from 1 to 20 parts by weight per 100 parts by weight of the whole polymerizable monomers, and is preferably added in an amount of from 2 to 15 parts by weight from the standpoint of effect.

Water may be added to the adhesive for directly restoring the teeth of the present invention to effectively improve the adhesion strength and, particularly, the adhesion strength to the enamel even though the pretreatment and the irradiation with light are not required. Addition of the water promotes the decalcification of the tooth tissue. Besides, use of the multi-valent ion-eluting filler in combination is particularly preferred since it promotes the chelate reaction. It is desired that the water does not substantially contain impurities which are detrimental to the preservation stability, adaptability to the living body and adhering property. Preferably, the water is the deionized water or the distilled water. The amount of addition may be 2 to 30 parts by weight and, preferably, 3 to 20 parts by weight per 100 parts by weight of the whole polymerizable monomers. When the amount of addition of water exceeds 30 parts by weight, the strength of the cured product drastically decreases, which is not desirable.

As the filler used for the adhesive for indirectly restoring the teeth of the invention, there can be used, without limitation, an inorganic filler, an organic filler and an inorganic/organic composite filler obtained by pulverizing the composite material of the inorganic oxide and a polymer, which are usually used for the dental adhesives.

Concrete examples of the inorganic filler that can be used for the adhesive for indirectly restoring the teeth of the invention include quartz, silica, silica-alumina, silica-titania, silica-zirconia, silica-magnesia, silica-calcia, silica-barium oxide, silica-strontium oxide, silica-titania-sodium oxide, silica-titania-potassium oxide, titania, zirconia and alumina. As the inorganic filler, the above-mentioned multi-valent ion-eluting filler, too, can be preferably used. Like those described above, the inorganic fillers may be treated with a surface treating agent as represented by a silane coupling agent.

Concrete examples of the organic filler that can be used for the adhesive for indirectly restoring the teeth of the present invention include polymethyl methacrylate, polyethyl methacrylate, methyl methacrylate-ethyl methacrylate copolymer, ethyl methacrylate-butyl methacrylate copolymer, methyl methacrylate-trimethylolpropane methacrylate copolymer, polyvinyl chloride, polystyrene, chlorinated polyethylene, nylon, polysulfone, polyethersulfone, and polycarbonate.

There is no particular limitation on the shape of the fillers; i.e., the fillers may be of a pulverized particulate shape as is usually obtained through pulverization or of a spherical particulate shape. There is no particular limitation even on the particle diameter of the fillers, but it is desired that the filler has a particle diameter of not larger than 100 $\mu$m and, more preferably, not larger than 30 $\mu$m from the standpoint of a film thickness for obtaining good adaptability.

The filler may be added in an amount of 50 to 900 parts by weight per 100 parts by weight of the whole polymerizable monomers. When the amount of addition is smaller than 50 parts by weight, physical strength of the material decreases. When the amount of addition is not smaller than 900 parts by weight, the fluidity of the material decreases to impair the operability. A more preferred amount of addition is from 100 to 800 parts by weight.

It is desired that the dental adhesive of the present invention is added with a catalyst for photo polymerization within a range in which it does not impair the properties. By using the catalyst for photo polymerization in combination, the adhesive can be used as the one of the dual curing-type which is cured either chemically or optically, finding an extended range of clinical applications, which is particularly desirable.

In addition to the above-mentioned components, the dental adhesive of the present invention may contain organic solvent, viscosity increasing agent, inorganic acid, organic acid, ultraviolet ray-absorbing agent, polymerization adjusting agent, dye, antistatic agent, pigment and perfume within a range in which they do not impair the effects of the invention.

As the organic solvent soluble in water, there can be used alcohols or ethers such as methanol, ethanol, propanol, butanol, ethylene glycol, propanediol, butanediol, pentanediol, butenediol, glycerin, trimethylolpropane, hexanetriol, allyl alcohol, diethylene glycol, diethylene glycol monomethyl ether, diethylene glycol monoethyl ether, triethylene glycol, triethylene glycol monomethyl ether, tetraethylene glycol, propylene glycol, dipropylene glycol, tripropylene glycol, 2-methoxyethanol, 2-ethoxyethanol, 2-(methoxyethoxy)ethanol, 2-isopropoxyethanol, 2-butoxyethanol, 1-methoxy-2-propanol, 1-ethoxy-2-propanol, dipropylene glycol monomethyl ether, tripropylene glycol monomethyl ether and glycerin ether; ketones such as acetone and methyl ethyl ketone; and carboxylic acids such as acetic acid, acetic anhydride and propionic acid. As the water-insoluble organic solvent, there can be used hexane, heptane, octane, toluene, dichloromethane, chloroform, carbon tetrachloride, dichloroethane, trichloroethane, pentanone, ethyl formate, propyl formate, butyl formate, ethyl acetate, propyl acetate, and butyl acetate. Among them, it is desired to use those having little beneficial/harmful action to the living body. Preferably, therefore, there are used ethanol, propanol, ethylene glycol, propanediol, butanediol, pentanediol, glycerin, trimethylolpropane, hexanetriol, diethylene glycol, diethylene glycol monomethyl ether, diethylene glycol monoethyl ether, triethylene glycol, triethylene glycol monomethyl ether, tetraethylene glycol, propyene glycol, dipropylene glycol, tripropylene glycol, dipropylene glycol monomethyl ether, tripropylene glycol monomethyl ether, glycerine ether, acetone and 2-hydroxyethyl methacrylate. Particularly preferably, there are used ethanol, propanol, ethylene glycol, propanediol and acetone. As required, these organic solvents may be used in plural kinds being mixed together.

As the viscosity-increasing agent, there can be used a polymer such as carboxymethyl cellulose or polyvinyl alcohol, and a highly dispersing silica.

As the inorganic acid, there can be used hydrochloric acid, sulfuric acid, nitric acid and phosphoric acid. As the organic acid, there can be used carboxylic acids such as acetic acid, propionic acid, maleic acid, fumaric acid, phthalic acid, benzoic acid, trichloroactic acid, trifluoroacetic acid, citric acid and trimellitic acid; sulfonic acids such as p-toluenesulfonic acid, benzenesulfonic acid, methanesulfonic acid and trifluoromethanesulfonic acid; and phosphoric acids such as methylphosphonic acid, phenylphosphonic acid, dimethylphosphinic acid and diphenylphosphinic acid.

It is desired that the adhesive of the present invention is packaged in a manner that the aryl borate compound is packaged separately from the acidic group-containing polymerizable monomer. The aryl borate compound undergoes the decomposition under acidic conditions. In the case of, for example, the bonding agent, therefore, a liquid chiefly comprising the acidic group-containing polymerizable monomer and other polymerizable monomers, is packaged separately from a liquid chiefly comprising the polymerizable monomer without containing acidic group, the organic peroxide and the aryl borate compound. In the case of the dental cement, the liquid chiefly comprising the acidic group-containing polymerizable monomer, other polymerizable monomers and the organic peroxide, is packaged separately from the powder chiefly comprising the filler and the aryl borate compound, or the paste chiefly comprising the acidic group-containing polymerzable monomer, the filler and the organic peroxide is packaged separately from the paste comprising the other polymerizable monomers, the filler and the aryl borate compound. At the time of use, these packages are mixed together.

Though there is no particular limitation, the adhesive of the present invention is desirably used in a manner as described below.

Namely, in the case of the adhesive for directly restoring the teeth (bonding agent), the dental curable composition that serves as the adhesive is applied onto the tooth surfaces by using a sponge or a small brush. Then, immediately or after left to stand for several seconds to a few minutes, a restorative such as the composite resin is filled and is cured by polymerization, so that the repairing material firmly adheres onto the dentin.

In the case of the adhesive for indirectly repairing the teeth (dental cement), the dental curable composition that serves as the adhesive is applied onto the tooth surfaces and/or onto various repairing materials directly by using a spatula or a small brush, so that the two are brought in contact to be cured by polymerization. In order to obtain a more strong adhering strength, the tooth surfaces may be treated in advance with an acidic aqueous solution or with the pretreatment material containing the acidic group-containing polymerizable monomer and water, followed by the above-mentioned adhering method. (II) Dental restorative of the invention.

The dental restorative of the present invention comprises a dental curable composition of the invention which contains a filler in an amount of from 50 to 900 parts by weight per 100 parts by weight of the whole polymerizable monomers. Here, the dental restorative stands for the one of which the cured product becomes a material, which substitutes for a damaged portion of the tooth, like a direct restorative such as composite resin, or like an indirect restorative that is used for forming an inlay, a crown or a bridge.

As the polymerizable monomer used for the dental restorative of the invention, there can be used, without limitation, the polymerizable monomer in the dental curable composition of the present invention.

As the filler for the dental restorative of the present invention, there can be used an inorganic filler or an organic filler depending upon the use without limitation. When used in combination with the inorganic filler, the dental restorative can be used as a composition such as a composite resin of the chemical polymerization type for filling or a composite resin for constructing a support. When used in combination with the organic filler, the dental restorative can be preferably used as a dental self-curing resin for curing at ambient temperature for forming a temporary crown or bridge.

As the inorganic filler, there can be preferably used those that were exemplified concerning the adhesive for indirectly restoring the teeth of the present invention. The inorganic fillers may be treated with a surface treating agent as represented by a silane coupling agent.

As the organic filler, there can be preferably used those that were exemplified concerning the adhesive for indirectly restoring the teeth of the present invention.

There is no particular limitation on the shape of the fillers which may have a pulverized particulate shape as obtained by an ordinary pulverization or may have a spherical particulate shape. Though there is no particular limitation on the diameter of the particles of the filler, the particles having a diameter of not larger than 100 $\mu$m are usually used from the standpoint of operability.

The amount of addition of the fillers varies depending upon the use and cannot be exclusively determined, but is selected in a range of from 50 to 900 parts by weight and, more preferably, from 100 to 800 parts by weight per 100 parts by weight of the whole polymerizable monomers.

The dental restorative of the present invention may contain the catalyst for photo polymerization in a range in which it does not impair the physical properties. By using the catalyst for photo polymerization in combination, the dental restorative can be used as the restorative of the dual curing-type which cures either chemically or optically, and finds a wide range of clinical applications, which is particularly preferable.

In addition to the above-mentioned components, the dental restorative of the present invention may contain viscosity increasing agent, inorganic acid, organic acid, ultraviolet ray absorber, polymerization adjusting agent, dye, antistatic agent, pigment and perfume in a range in which they do not impair the effect of the invention. As these components, there can be preferably used those exemplified concerning the dental adhesive of the present invention.

As described earlier, the aryl borate compound is subject to be decomposed under acidic conditions. In packaging the dental restorative of the present invention, therefore, it is desired that the aryl borate compound, the acidic group-containing polymerizable monomer and the organic peroxide are packaged separately from each other and are brought in contact with one another at the time of use. For example, the liquid chiefly comprising the polymerizable monomer, the acidic compound and the organic peroxide is packaged separately from the liquid chiefly comprising the polymerizable monomer and the aryl borate compound. They are mixed together just before being used. (III) Dental pretreatment material of the invention.

The dental pretreatment material of the invention comprises a dental curable composition of the invention containing the acidic group-containing polymerizable monomer, the aryl borate compound, the organic peroxide and water.

The acidic group-containing polymerizable monomer used for the dental pretreatment material of the present invention also works as an acidic compound of the dental catalyst for chemical polymerization of the invention. As the acidic group-containing polymerizable monomer, there can be used those described above as the acidic compounds without limitation. From the standpoint of adhering strength to the tooth tissue or to the base metal, however, it is desired to use the acidic group-containing polymerizable monomer same as the one described above to be preferably used for the adhesive of the invention. By using the phosphoric acid group-containing polymerizable monomer in combination with the multi-valent carboxylic acid group-containing polymerizable monomer having plural carboxylic acid groups in a molecule, further, there is realized a highly increased adhesion to the dentin with little dispersion in the adhering strength like the adhesive of the present invention.

The blending amount of the acidic group-containing polymerizable monomer in the pretreatment material of the present invention is, preferably, from 3 to 50% by weight and, more preferably, from 7 to 40% by weight per 100% by weight of the whole components constituting the pretreatment material composition. When the blending amount is smaller than 3% by weight, the adhering strength to the enamel is not sufficient. When the adhering strength is not smaller than 50% by weight, the adhering strength to the dentin and to the enamel decreases.

The aryl borate compound used for the pretreatment material of the present invention is one of the components of the dental catalyst for chemical polymerization of the present invention, and those described above can be used without limitation. The amount of addition of the aryl borate compound may differ depending upon the kinds and blending ratios of other components, but is preferably, from 0.01 to 10% by weight, more preferably from 0.05 to 8% by weight and, most preferably, from 0.5 to 6% by weight per 100% by weight of the whole components constituting the pretreatment material composition.

The organic peroxide used for the pretreatment material of the present invention is one of the components of the dental catalyst for chemical polymerization of the invention, and those described above can be used without limitation. The amount of the organic peroxide is used is preferably from 0.01 to 10% by weight, more preferably, from 0.05 to 8% by weight and, most preferably, from 0.5 to 5% by weight per 100% by weight of the whole components constituting the pretreatment material to obtain excellent effect of adhesion. When the amount of addition is smaller than 0.01% by weight, the catalyst for polymerization exhibits decreased effect and, hence, the adhering strength decreases to both the enamel and the dentin. When the amount exceeds 10% by weight, a problem arouses concerning the preservation stability of the composition.

It is further desired to add the above-mentioned decomposition promoting agent to the dental pretreatment material of the present invention to further increase the adhesiveness.

Water used for the pretreatment material of the present invention is necessary for decalcification of the tooth tissue. It is desired that the water does not substantially contain impurities detrimental to preservation stability, adaptability to living bodies and adhesiveness, and it is desired to use, for example, the deionized water or the distilled water. A preferred amount of addition of water is from 5 to 90% by weight and, more desirably, from 20 to 80% by weight per 100% by weight of the whole components constituting the pretreatment material composition. When the amount is smaller than 5% by weight, the tooth tissue cannot be decalcified to a sufficient degree, and the adhering strength becomes insufficient to both the enamel and the dentin. When the amount exceeds 90% by weight, the adhering strength tends to decrease to both the dentin and the enamel.

In addition to the above-mentioned components, the dental pretreatment material of the present invention may contain water-soluble organic solvent, water-insoluble organic solvent, polymerizable monomers other than the acidic group-containing polymerizable monomers, other catalysts for polymerization, inorganic strong acid and metal salt within a range in which they do not impair the effect of the invention. The additives that can be used are the same as those described above as additives for the adhesives of the present invention.

When the acidic group-containing polymerizable monomer that is used does not easily dissolve in water, the components are dissolved in a water-soluble organic solvent to obtain a homogeneous solution or an emulsion that remains stable for a long period of time to a degree that does not pose problem. The water-soluble organic solvents that can be used here may be the same as those exemplified for the adhesives of the present invention. Among them, it is desired to use those exemplified to exhibit less beneficial/harmful action and, particularly, alcohols such as ethanol. The water-soluble organic solvents can, as required, be used in plural kinds being mixed together. It is desired that the amount of blending the water-soluble organic solvents is not larger than 80% by weight in the whole components constituting the pretreatment material.

There is no particular limitation on the method of using the dental pretreatment material of the present invention. Preferably, the acidic group-containing polymerizable monomer, organic peroxide, aryl borate compound, water and any components that are blended as required, are weighed and put into a container at a desired ratio, are stirred and mixed together to obtain a homogeneous solution or an emulsion which is, then, applied to the tooth surfaces by using a sponge or a small brush, left to stand for several seconds to a few minutes, and is dried by blowing the air thereto. Thereafter, the adhesive is applied onto the pretreated tooth surfaces, and various restoratives are brought into contact therewith to cure the adhesive by polymerization. The components constituting the dental pretreatment material of the invention may be used in a separate manner. For example, the pretreatment is effected with a solution containing the acidic group-containing polymerizable monomer followed by the treatment with a solution containing the organic peroxide, water and aryl borate compound. In this case, the curable composition of the present invention is formed on the tooth surfaces. A uniform film is formed on the surfaces of the tooth after the treatment with the dental pretreatment material of the invention, and the components of the adhesive that is applied later diffuse into the film accounting for a favorable adhesion to the tooth tissue.

Here, as described earlier, the aryl borate compound easily undergoes the decomposition under the acidic conditions. Desirably, therefore, the dental pretreatment material of the present invention is packaged in a divided manner, so that the aryl borate compound, the acidic group-containing polymerizable monomer and the organic peroxide are brought into contact with each other for the first time at the time of use. For example, the solution chiefly comprising the acidic group-containing polymerizable monomer, oxidizing agent such as organic peroxide and other components is prepared separately from the solution chiefly comprising the water and the aryl borate compound. These solutions are separately packaged and are mixed together just before the use.

EXAMPLES

The present invention will now be concretely described with reference to Examples to which only, however, the invention is in no way limited.

The compounds and their abbreviations used in Examples and in Comparative Examples are described in (1), the method of measuring the curing time is described in (2), the methods of measuring properties of various cured products are described in (3) to (6), the method of measuring the adhering strength of the adhesive for directly restoring the teeth of the invention is described in (7), the method of measuring the adhering strength of the adhesive for indirectly restoring the teeth of the invention is described in (8), and the method of measuring the adhering strength using the dental pretreatment material of the invention is described in (9). (1) Abbreviations and structures.

[Acidic Group-Containing Polymerizable Monomers]

| | |
|---|---|
| PM; | A mixture of 2-methacryloyloxyethyldihydrogen phosphate and bis(2-methacryloyloxyethyl)hydrogen phosphate. |
| MAC-10; | 11-Methacryloyloxy-1,1-undecanedicarboxylic acid. |
| 4-META; | 4-Methacryloyloxyethyltrimellitic anhydride. |
| MTS; | 2-Methacryloyloxyethyl-3'-methacryloyloxy-2'-(3,4-dicarboxybenzoyloxy)propyl succinate. |

[Polymerizable Monomers other than the Acidic Group-Containing Polymerizable Monomers]

| | |
|---|---|
| MMA; | Methyl methacrylate. |
| TMPT; | Trimethylolpropane trimethacrylate. |
| bis-GMA; | 2,2-Bis[4-(2-hydroxy-3-methacryloyloxypropoxy)phenyl]propane. |
| 3G; | Triethylene glycol dimethacrylate. |
| D2.E6; | 2,2-Bis[(4-methacryloyloxypolyethoxyphenyl)propane] |
| HEMA; | 2-hydroxyethyl methacrylate. |
| MTU-6; | 6-Methacryloyloxyhexyl-2-thiouracil-5-carboxylate. |
| NPG; | Neopentyl glycol dimethacrylate |

[Organic Peroxides]

| | |
|---|---|
| Permek N; | Methyl ethyl ketone peroxide. |
| Perhexa H; | Cyclohexanone peroxide. |
| Perhexyl H; | t-Hexyl hydroperoxide. |
| Percumyl P; | Diisopropylbenzene hydroperoxide. |
| Perbutyl H; | t-butyl hydroperoxide. |
| BPO; | Benzoyl peroxide. |
| Perhexyl I; | t-Hexyl peroxyisopropyl monocarbonate. |
| Perbutyl I; | t-Butyl peroxyisopropyl monocarbonate. |
| Percumyl H; | Cumene hydroperoxide. |
| Perbutyl D; | Di-t-butyl peroxide. |

[Borate Compounds]

| | |
|---|---|
| PhBNa; | Sodium tetraphenylborate. |
| PhBTEOA; | Tetraphenylboron triethanolamine salt. |
| PhBDMPT; | Tetraphenylboron dimethyl-p-toluidine salt. |
| PhBDMBE; | Tetraphenylboron ethyl dimethylaminobenzoate salt. |
| FPhBNa; | Sodium tetrakis(p-fluorophenyl)borate. |
| PhBTEA; | Tetraphenylboron triethylamine salt. |
| PhBDMEM; | Tetraphenylboron dimethylaminoethyl methacrylate salt. |
| PhBDEA; | p-Diethylaminoacetophenonetetraphenyl borate. |
| PhBDEPT; | Tetraphenylboron diethyl-p-toluidine salt. |

[Decomposition Promoting Agents]

| | |
|---|---|
| FeAA; | Iron (III) acetylacetonato. |
| CuAA; | Copper (II) acetyacetonato. |
| $FeCl_3$; | Iron chloride (III). |

[Fillers]

| | |
|---|---|
| PEMA; | Polyethyl methacrylate. |
| P(MMA-EMA); | Methyl methacrylate-ethyl methacrylate copolymer. |
| 0.5Si-Zr; | Spherical silica-zirconia of which the surfaces are treated with γ-methacryloyloxypropyltrimethoxysilane, average particle diameter, 0.5 μm. |
| 0.06Si-Zr; | Spherical silica-zirconia of which the surfaces are treated with γ-methacryloyloxypropyltrimethoxysilane, average particle diameter, 0.06 μm. |
| FASG; | Fluoroaluminosilicate glass powder. |
| PMMA; | Polymethyl methacrylate. |
| 3Si-Zr; | Amorphous silica-zirconia of which the surfaces are treated with γ-methacryloyloxypropyltrimethoxysilane, average particle diameter, 3 μm. |
| 0.3Si-Ti; | Spherical silica-titania of which the surfaces are treated with γ-methacryloyloxypropyltrimethoxysilane, average particle diameter, 0.3 μm. |

-continued

[Other Components]

| | |
|---|---|
| DEPT; | p-Tolyldiethanolamine. |
| TCT; | 2,4,6-tris(trichloromethyl)-s-triazine. |
| DMPT; | Dimethylamino-p-toluidine. |
| CDAC; | 3,3'-carbonylbis(7-diethylamino)cumarin. |
| BAPO; | Bis(2,4,6-trimethylbenzoyl)-phenylphosphine oxide. |
| BDTPO; | Bis(2,6-dimethoxybenzoil)-2,4,4-trimethylpentylphosphine oxide. |
| IPA; | Isopropyl alcohol. |

(2) Measurement of Curing Time.

The curing time was measured relying on the exothermic method by using a thermistor thermometer. That is, (a) 5 g of a polymerizable monomer solution containing an organic peroxide and an acidic compound and (b) 5 g of a polymerizable monomer solution containing an aryl borate compound, were stirred and mixed together for 20 seconds to prepare a homogeneous solution. The solution was then poured into a Teflon mold measuring 2 cm×2 cm×1 cm having a hole of a diameter of 6 mm at the center thereof. The thermistor thermometer was inserted in the hole, and the time from the start of the mixing until when a maximum temperature was recorded was regarded to be the curing time. The measurement was taken in a constant-temperature room maintained at 23° C.

(3) Evaluation of Curing Property and Surface Stickiness

Curable compositions were prepared in the same manner as described above, poured into the molds of the same shape, and were cured in the air at 23° C. for 15 minutes. The hardness and the surface stickiness of the cured products were evaluated in five stages. That is, the cured products having a sufficient degree of hardness without surface stickiness were evaluated to be ⊚, the products having a sufficient degree of hardness but with sticky surfaces were evaluated to be ○, the products which were like a jelly with unpolymerized monomer remaining on the surfaces were evaluated to be Δ, the products which were partly in a jelly-like consistency were regarded to be X, and the products which were not cured at all were regarded to be X X.

(4) Testing the Initial Color and Resistance against Discoloration of the Cured Products The resistance against discoloration of the cured products was tested in a manner as described below. That is, the components were mixed together at a predetermined ratio and were kneaded for 20 seconds. The mixture was then poured into a mold measuring 10 mm×10 mm×2 mm, and was cured at 37° C. for 24 hours. The initial colors of the cured products were evaluated by eyes in three stages as follows:

Score 1: Colorless and transparent.
Score 2: Yellow.
Score 3: Brown.

The obtained cured products were preserved in water maintained at 80° C. for 60 days, and the degree of discoloration of the cured products after preserved was evaluated in compliance with the following reference of evaluation.

Score 1: No change.
Score 2: Cloudy.
Score 3: Discolored into a pale yellow.
Score 4: Discolored into yellow.
Score 5: Discolored into brown.

(5) Measurement of Bending Strength and Hardness

The bending strength of the cured products was measured in a manner as described below. First, the components were homogeneously mixed together at a predetermined ratio, poured into a mold measuring 25 mm×4 mm×2 mm, and were cured at 37° C. for 24 hours. The obtained cured product was put to the bend break-down testing over a distance of 20 mm between the fulcrums. The crosshead speed was 1 mm/min. For measuring the hardness, the surfaces of the cured product were buffed, and the Knoop hardness was measured under the load of 10 g for 20 seconds by using a microhardness tester manufactured by Matsuzawa Seiki Co. The measurement was taken in a constant-temperature room maintained at 23° C.

(6) Measurement of the Amount of the Residual Monomer

The amounts of residual monomers in the cured products were measured in a manner as described below. First, the components were mixed together at a predetermined ratio, poured into a mold measuring 20 mm×20 mm×1 mm, and were cured at 37° C. for 24 hours. The obtained cured product was immersed in acetonitrile at 23° C. for 24 hours, and the amount of the monomer in the solution was determined by a high-performance liquid chromatography.

Example 1

Into 100 parts by weight of an MMA/TMPT (90 wt %/10 wt %) solution were added 4 parts by weight of the Permek N as an organic peroxide and 5 parts by weight of PM as an acidic compound to prepare a homogeneous solution (a) thereof. Separately, to the MMA/TMPT (90 wt %/10 wt %) solution was added 3 parts by weight of PhBNa as an aryl borate compound to prepare a homogeneous solution (b) thereof. The two solutions were mixed together at a weight ratio of 1:1 so as to become homogeneous, and the curing time, curing property and surface stickiness were evaluated. The initial color and resistance against discoloration of the obtained cured products were also evaluated. The results were as shown in Table 1.

Examples 2 to 24

The MMA/TMPT (90 wt %/10 wt %) solutions containing the catalysts for chemical polymerization shown in Table 1 were prepared and were cured by the same method as that of Example 1 to measure the properties. The results were as shown in Table 1.

In all Examples, the cured products exhibited favorable results concerning the curing property and the surface stickiness without initial color of the cured products and with no or very little discoloration after preservation.

Examples 25 to 28

The MMA/TMPT (90 wt %/10 wt %) solutions containing the catalysts for chemical polymerization shown in Table 1 glib were prepared and were cured by the same method as that of Example 1 to measure the properties. The results were as shown in Table 1.

In these Examples, the agent was added for promoting the decomposition of the organic peroxide, and a further enhanced curing activity was exhibited. The cured products exhibited favorable results concerning the curing property and the surface stickiness without initial color of the cured products and with no or very little discoloration after preservation.

Comparative Examples 1 to 4

The MMA/TMPT (90 wt %/10 wt %) solutions containing the catalysts for chemical polymerization shown in Table 1 were prepared and were cured by the same method as that of Example 1 to measure the properties. The results were as shown in Table 1.

Comparative Examples 1 to 3 were the cases where there was not added one component among the essential components of the catalyst for chemical polymerization of the invention. Curing did not at all take place in Comparative Examples 1 and 2. In Comparative Example 3, the curing took place requiring, however, an extended period of time. Besides, what took place was a partial jelly-like consistency.

Comparative Example 4 was a case of using the conventional BPO/DMPT catalyst for chemical polymerization. The cured product was more sticky than those of Examples, exhibited an initial color, and was greatly discolored after preservation.

Examples 29 to 34

Powder components and liquid components were prepared to obtain compositions shown in Table 2. They were the compositions of the dental restoratives of the invention. The powders and liquids were kneaded at a ratio of 2/1 to examine the curing times, bending strengths of the cured products, Knoop hardnesses, amounts of the residual monomers and resistances against discoloration of the cured products. The results were as shown in Table 3.

Comparative Example 5

Properties were measured in the same manner as in Examples 29 to 34 but preparing the powder components and the liquid components to obtain compositions shown in Table 2. The results were as shown in Table 3.

Comparative Example 5 was the case of using the BPO/DEPT as a catalyst for chemical polymerization. In this case, however, the amount of the residual monomer was larger than those of Examples, and the discoloration of the cured product was conspicuous, too.

Examples 35 to 40

Two kinds of paste components were prepared to obtain compositions shown in Table 4. They were the compositions of the dental restoratives of the invention. The powders were kneaded at a weight ratio of 1/1 to examine the curing times, bending strengths of the cured products, Knoop hardnesses, and resistances against discoloration of the cured products. The results were as shown in Table 5.

Comparative Example 6

Properties were measured in the same manner as in Examples 35 to 40 with the exception of preparing the two kinds of paste components to obtain compositions shown in Table 4. The results were as shown in Table 5.

Comparative Example 6 was the case of using the BPO/DEPT as a catalyst for chemical polymerization. In this case, however, the discoloration of the cured products was conspicuous.

TABLE 1

| Ex. No. | Organic peroxide (parts by wt.) | | Aryl borate Compound (parts by wt.) | | Acidic compound (parts by wt.) | | Decomposition promoter (parts by wt.) | | Curing time | Curing property, surface stickiness | Initial color | Resistance to discoloration |
|---|---|---|---|---|---|---|---|---|---|---|---|---|
| 1 | Permek N | (4) | PhBNa | (3) | PM | (5) | — | — | 3'20" | ◎ | 1 | 1 |
| 2 | Permek N | (4) | PhBNa | (1) | PM | (5) | — | — | 7'00" | ◎ | 1 | 1 |
| 3 | Permek N | (2) | PhBNa | (3) | PM | (5) | — | — | 4'40" | ◎ | 1 | 1 |
| 4 | Perhexa H | (2) | PhBNa | (1) | PM | (5) | — | — | 10'30" | ◎ | 1 | 1 |
| 5 | Perhexa H | (4) | PhBNa | (3) | PM | (5) | — | — | 3'30" | ◎ | 1 | 1 |
| 6 | Perhexyl H | (4) | PhBNa | (3) | PM | (5) | — | — | 2'50" | ◎ | 1 | 1 |
| 7 | Percumyl P | (4) | PhBNa | (3) | PM | (5) | — | — | 2'40" | ◎ | 1 | 1 |
| 8 | Perbutyl H | (4) | PhBNa | (3) | PM | (5) | — | — | 2'40" | ◎ | 1 | 1 |
| 9 | Perbutyl D | (4) | PhBNa | (3) | PM | (5) | — | — | 4'30" | ◎ | 1 | 1 |
| 10 | BPO | (4) | PhBNa | (3) | PM | (5) | — | — | 5'20" | ○ | 1 | 1 |
| 11 | Perhexyl I | (4) | PhBNa | (3) | PM | (5) | — | — | 8'50" | ◎ | 1 | 1 |
| 12 | Perbutyl I | (4) | PhBNa | (3) | PM | (5) | — | — | 6'40" | ◎ | 1 | 1 |
| 13 | Percumyl H | (4) | PhBNa | (3) | PM | (5) | — | — | 2'30" | ◎ | 1 | 1 |
| 14 | Percumyl H | (4) | PhBNa | (3) | phosphoric acid | (5) | — | — | 4'00" | ○ | 1 | 1 |
| 15 | Percumyl H | (4) | PhBNa | (3) | nitric acid | (5) | — | — | 3'40" | ○ | 1 | 1 |
| 16 | Percumyl H | (4) | PhBNa | (3) | nitric acid | (5) | — | — | 3'40" | ○ | 1 | 1 |
| 17 | Percumyl H | (4) | PhBTEOA | (3) | PM | (5) | — | — | 2'50" | ◎ | 1 | 1 |
| 18 | Percumyl H | (4) | PhBDMPT | (3) | PM | (5) | — | — | 3'00" | ◎ | 1 | 2 |
| 19 | Percumyl H | (4) | PhBDMBE | (3) | PM | (5) | — | — | 2'40" | ◎ | 1 | 1 |
| 20 | Percumyl H | (4) | PhBDEPT | (3) | PM | (5) | — | — | 2'50" | ◎ | 1 | 1 |
| 21 | Percumyl H | (4) | FPhBNa | (3) | PM | (5) | — | — | 3'10" | ◎ | 1 | 1 |
| 22 | Percumyl H | (4) | PhBTEA | (3) | PM | (5) | — | — | 2'30" | ◎ | 1 | 2 |
| 23 | Percumyl H | (4) | PhBDMEM | (3) | PM | (5) | — | — | 3'00" | ◎ | 1 | 1 |
| 24 | Percumyl H | (4) | BFPhBNa | (3) | PM | (5) | — | — | 2'00" | ◎ | 1 | 1 |
| 25 | Percumyl H | (4) | PhBTEOA | (3) | PM | (5) | FeAA | (0.005) | 2'10" | ◎ | 1 | 1 |
| 26 | Percumyl H | (4) | PhBDEA | (3) | PM | (5) | CuAA | (0.005) | 2'40" | ◎ | 1 | 1 |
| 27 | Percumyl H | (4) | PhBDEA | (3) | PM | (1) | FeAA | (0.005) | 4'30" | ◎ | 1 | 1 |
| 28 | Percumyl H | (4) | PhBDEA | (3) | phosphoric acid | (1) | FeAA | (0.005) | 4'50" | ◎ | 1 | 1 |
| Comp. Ex. | | | | | | | | | | | | |
| 1 | Permek N | (4) | PhBNa | (3) | — | (5) | — | — | — | — | — | — |
| 2 | Permek N | (4) | — | (3) | PM | (5) | — | — | — | — | — | — |
| 3 | — | — | PhBNa | (3) | PM | (5) | — | — | >40'00" | × | 1 | — |
| 4 | BPO | (4) | DEPT | (2) | — | — | — | — | 3'00" | ○ | 2 | 5 |

TABLE 2

| Ex. NO. | Powder component | | | | Liquid component | | | | | |
|---|---|---|---|---|---|---|---|---|---|---|
| | Filler (parts by wt) | | Aryl. borate compound (Parts by wt.) | Decomposition promoter (parts by wt.) | Polymrtizable number (parts by wt.) | | Organic peroxide (parts by wt.) | | Acidic compound (parts by wt.) | |
| 29 | PEMA P(MMA-EMA) | (5) (95) | PhBNa (3) | — | MMA TMPT | (90) (10) | Percumyl H | (2) | PM | (5) |
| 30 | PEMA P(MMA-ENA) | (5) (95) | PhBTEOA (3) | — | MMA TMPT | (90) (10) | Percumyl H | (2) | PM | (5) |
| 31 | PEMA P(MMA-EMA) | (5) (95) | PhBTEOA (3) | — | MMA TMPT | (90) (10) | Permek N | (2) | PM | (5) |
| 32 | PEMA P(MMA-EMA) | (5) (95) | PhBTEOA (3) | — | MMA TMPT | (90) (10) | Perbutyl H | (2) | PM | (5) |
| 33 | PEMA P(MMA-EMA) | (5) (95) | PhBTEOA (3) | FeAA (0.005) | MMA TMPT | (90) (10) | Percumyl H | (2) | PM | (5) |
| 34 | PEMA P(MMA-EMA) | (5) (95) | PhBTEOA (3) | CuAA (0.005) | MMA TMPT | (90) (10) | Percumyl H | (2) | PM | (5) |
| Comp. Ex. | | | | | | | | | | |
| 5 | PEMA P(MMA-EMA) | (5) (95) | Organic peroxide (2) BPO | — | MMA TMPT | (90) (10) | Amine compound | (3) | — | |

TABLE 3

| | Curing time (sec) | Bending strength (MPa/cm²) | Knoop hardness (Hk) | Amount of residual monomer (%) | Score of discoloration resistance |
|---|---|---|---|---|---|
| Ex. 29 | 3'00" | 98 | 14.6 | 1.1 | 1 |
| Ex. 30 | 2'50" | 100 | 14.7 | 1.2 | 1 |
| Ex. 31 | 2'50" | 105 | 14.1 | 1.1 | 1 |
| Ex. 32 | 3'10" | 103 | 14.8 | 1.4 | 1 |
| Ex. 33 | 2'30" | 108 | 15.0 | 1.0 | 1 |
| Ex. 34 | 2'40" | 106 | 14.9 | 1.0 | 1 |
| Comp. Ex. 5 | 3'00" | 95 | 13.0 | 3.2 | 4 |

TABLE 4

<Paste (a)>

| Sample No. | Filler (Parts by wt.) | | Polymerizable monomer (parts by wt.) | | Organic peroxide (parts by wt.) | Acidic compound (parts by wt.) | |
|---|---|---|---|---|---|---|---|
| Ex. 35 | 0.5Si-Zr | (70) | bis-GMA | (35) | Percumyl H (1) | PM | (5) |
| | 0.06Si-Zr | (30) | 3G | (23) | | | |
| Ex. 36 | 0.5Si-Zr | (70) | bis-GMA | (35) | Percumyl H (1) | PM | (5) |
| | 0.06Si-Zr | (30) | 3G | (23) | | | |
| Ex. 37 | 0.5Si-Zr | (70) | bis-GMA | (35) | Permek N (1) | PM | (5) |
| | 0.06Si-Zr | (30) | 3G | (23) | | | |
| Ex. 38 | 0.5Si-Zr | (70) | bis-GMA | (35) | Perbutyl H (1) | PM | (5) |
| | 0.06Si-Zr | (30) | 3G | (23) | | | |
| Ex. 39 | 0.5Si-Zr | (70) | bis-GMA | (35) | Percumyl H (1) | PM | (5) |
| | 0.06Si-Zr | (30) | 3G | (23) | | | |
| Ex. 40 | 0.5Si-Zr | (70) | bis-GMA | (35) | Percumyl H (1) | PM | (5) |
| | 0.06Si-Zr | (30) | 3G | (23) | | | |
| Comp. Ex. 6 | 0.5Si-Zr | (70) | bis-GMA | (35) | BPO (2) | — | — |
| | 0.06Si-Zr | (30) | 3G | (23) | | | |

<Paste (b)>

| Sample No. | Filler (Parts by wt.) | | Polymerizable monomer (parts by wt.) | | Aryl borate compound (parts by wt.) | Decomposition promoter (parts by wt.) | |
|---|---|---|---|---|---|---|---|
| Ex. 35 | 0.5Si-Zr | (70) | bis-GMA | (40) | PhETEOA (3) | — | — |
| | 0.06Si-Zr | (30) | 3G | (27) | | | |
| Ex. 36 | 0.5Si-Zr | (70) | bis-GMA | (40) | FphBNa (3) | — | — |
| | 0.06Si-Zr | (30) | 3G | (27) | | | |
| Ex. 37 | 0.5Si-Zr | (70) | bis-GMA | (40) | PhBTEOA (3) | — | — |
| | 0.06Si-Zr | (30) | 3G | (27) | | | |
| Ex. 38 | 0.5Si-Zr | (70) | bis-GMA | (40) | PhBTEOA (3) | — | — |
| | 0.06Si-Zr | (30) | 3G | (27) | | | |
| Ex. 39 | 0.5Si-Zr | (70) | bis-GMA | (40) | PhBTEOA (3) | CuAA | (0.005) |
| | 0.06Si-Zr | (30) | 3G | (27) | | | |
| Ex. 40 | 0.5Si-Zr | (70) | bis-GMA | (40) | PhBTEOA (3) | FeAA | (0.005) |
| | 0.06Si-Zr | (30) | 3G | (27) | | | |
| Comp. Ex. 6 | 0.5Si-Zr | (70) | bis-GMA | (40) | amine compound | — | — |
| | 0.06Si-Zr | (30) | 3G | (27) | DEPT (3) | | |

TABLE 5

| | Curing time (sec) | Bending strength (MPa/cm²) | Knoop hardness (Hk) | Score of discoloration resistance |
|---|---|---|---|---|
| Ex.35 | 3'10" | 117 | 36 | 1 |
| Ex.36 | 2'40" | 120 | 36 | 1 |
| Ex.37 | 3'00" | 118 | 37 | 1 |
| Ex.38 | 3'00" | 110 | 36 | 1 |
| Ex.39 | 2'40" | 121 | 37 | 1 |
| Ex.40 | 2'50" | 120 | 37 | 1 |
| Comp.Ex.6 | 2'40" | 100 | 35 | 4 |

(7) Measurement of Adhering Strengths of the Adhesives for Directly Restoring the Teeth (Bonding Agent) of the Present Invention A bovine foretooth was pulled out from the lower jaw within 24 hours after the slaughter, and the enamel or the dentin were ground flat to be in parallel with the lip surface by using a #800 emery paper while pouring water. The compressed air was blown to the surface for about 10 seconds to dry it, and a double-sided tape having a hole of a diameter of 3 mm was secured to the surface to specify the adhering area. Then, a wax of a thickness of 1 mm having a hole of a diameter of 8 mm was stuck to the double-sided tape to be in concentric therewith thereby to form a mimic cavity. A bonding agent prepared just before the use was applied into the mimic cavity and was left to stand for 20 seconds.

When the photo-curable composite resin was used, the mimic cavity was filled with the photo-curable composite resin, Palfique Estelite [manufactured by Tokuyama Co.], was covered with a polypropylene sheet, and was irradiated with light by using Power Light [manufactured by Tokuyama Co.] for 30 seconds to cure the composite resin by polymerization thereby to prepare a test piece.

When the chemically-curable composite resin was used, the mimic cavity was similarly filled with the chemically polymerizable composite resin, Palfique [manufactured by Tokuyama Co.] and was cured to prepare a test piece.

The test piece prepared by the above method was immersed in water maintained at 37° C. for 24 hours and was, then, put to the tensile testing by using a tensile tester (Autograph AG5000 manufactured by Shimadzu Co.) under a condition of a crosshead speed of 1 mm/min. Eight adhesion test pieces were measured per a test, and an average value thereof was regarded to be the adhering strength.

TABLE 6

| Liquid composition | First liquid composition (parts by wt.) | | | | | | | | | | | |
|---|---|---|---|---|---|---|---|---|---|---|---|---|
| | Acidic group-containing polymerizable monomer | | | Other polymerizable monomers | | | | | Decomposition promoter | | Organic peroxide | Photo acid generator |
| No. | PM | MAC-10 | 4-META | D2.6E | TMPT | MMA | bis-GMA | 3G | FeCl3 | CuAA | BPO | TCT |
| A | 30 | — | — | 15 | 5 | — | — | — | — | — | — | — |
| B | 20 | 10 | — | 15 | 5 | — | — | — | — | — | — | — |
| C | 20 | — | 10 | 15 | 5 | — | — | — | — | — | — | — |
| D | 20 | 10 | — | — | 5 | — | 6 | 9 | — | — | — | — |
| E | 20 | 20 | — | 10 | 5 | 5 | — | — | — | — | — | — |
| F | 20 | 10 | — | 15 | 5 | — | — | — | 0.005 | — | — | — |
| G | 20 | 10 | — | 15 | 5 | — | — | — | — | 0.005 | — | — |
| H | 20 | 9 | — | 15 | 5 | — | — | — | — | — | — | 1 |
| I | 20 | 9 | — | 15 | 5 | — | — | — | — | 0.005 | — | 1 |
| J | — | — | — | 30 | 10 | 10 | — | — | — | — | — | — |
| K | — | — | — | 29 | 10 | 10 | — | — | — | — | — | 1 |
| L | 20 | 9 | — | 15 | 5 | — | — | — | — | — | 1 | — |

TABLE 7

| Liquid composition | Second liquid composition | | | | | | | | |
|---|---|---|---|---|---|---|---|---|---|
| | Polymerizable Monomer | | Organic peroxide | | Aryl borate | | Others (parts | Amine (parts | Photo sensitzied dye |
| | (parts by wt.) | | parts by | | parts | | by wt.) | by wt.) | parts by wt.) |
| No. | HRMA | MMA | Compound | weight | Compound | by wt. | FASG Water | DMPT | CDAC |
| a | 32 | 14 | Percumyl H | 1 | PhBTEOA | 3 | — — | — | — |
| b | 32 | 8 | Percumyl H | 1 | PhBTEOA | 3 | 6 — | — | — |
| c | 27 | 14 | Percumyl H | 1 | PhBTEOA | 3 | — 5 | — | — |
| d | 27 | 8 | Percumyl H | 1 | PhBTEOA | 3 | 6 5 | — | — |
| e | 27 | 8 | Perhexa H | 1 | PhETEQA | 3 | 6 5 | — | — |
| f | 27 | 8 | Perbutyl H | 1 | PhBTEOA | 3 | 6 5 | — | — |
| g | 27 | 8 | Perbutyl D | 1 | PhBTEOA | 3 | 6 5 | — | — |
| h | 27 | 8 | Perhexyl I | 1 | PhBTEOA | 3 | 6 5 | — | — |
| i | 27 | 8 | Percumyl H | 1 | PhBNa | 3 | 6 5 | — | — |
| j | 27 | 8 | Percumyl H | 1 | PhBDMPT | 3 | 6 5 | — | — |
| k | 27 | 14 | Percumyl H | 1 | PhBDMEM | 3 | — 5 | — | — |
| l | 32 | 8 | Percumyl H | 1 | FPhBNa | 3 | 6 — | — | — |
| m | 27 | 8 | Percumyl H | 1 | PhBDEA | 3 | 6 5 | — | — |
| n | 26.99 | 8 | Percumyl H | 1 | PhBTEOA | 3 | 6 5 | — | 0.01 |
| o | 26.99 | 8 | Perhexa H | 1 | PhBTEOA | 3 | 6 5 | — | 0.01 |
| p | 26.99 | 8 | Percumyl H | 1 | PhBNa | 3 | 6 5 | — | 0.01 |
| q | 27 | 9 | — | — | PhBTEOA | 3 | 6 5 | — | — |
| r | 29 | 9 | Percumyl H | 1 | — | — | 6 5 | — | — |
| s | 26.99 | 9 | — | — | PhBTEOA | 3 | 6 5 | — | 0.01 |
| t | 28.99 | 9 | Percumyl H | 1 | — | — | 6 5 | — | 0.01 |
| u | 27 | 9 | — | — | — | — | 6 5 | 3 | — |

Example 41

There were separately prepared a first liquid composition A comprising 3 g of PM, 1.5 g of D2.6E and 0.5 g of TMPT, and a second liquid composition a comprising 3.2 g of HEMA, 1.4 g of MMA, 0.1 g of percumyl H and 0.3 g of PhBTEOA. Just before the use, the first liquid and the second liquid were mixed at a ratio of 1:1 to prepare a bonding agent. By using this bonding agent, the adhering strength was measured in compliance with the method of using the photo-curable composite resin. The results were as shown in Table 8. The adhering strength was 13.1 (1.8) MPa to the enamel and was 12.0 (2.1) MPa to the dentin [numerals in parentheses are standard deviations].

TABLE 8

| | Bonding agent composition | | | |
|---|---|---|---|---|
| | First liquid composition | Second liquid composition | Adhering strength/MPa(S.D.) | |
| | | | Enamel | Dentin |
| Ex.41 | A(50) | a(50) | 13.1(1.8) | 12.0(2.1) |
| Ex.42 | A(50) | b(50) | 14.1(2.3) | 15.6(1.6) |
| Ex.43 | A(50) | c(50) | 15.9(3.1) | 13.1(2.4) |
| Ex.44 | A(50) | d(50) | 16.8(2.0) | 15.7(1.9) |
| Ex.45 | B(50) | a(50) | 13.0(2.6) | 12.8(0.8) |
| Ex.46 | B(50) | b(50) | 14.3(1.9) | 17.1(1.5) |
| Ex.47 | B(50) | c(50) | 17.3(1.6) | 16.8(4.3) |
| Ex.48 | B(50) | d(50) | 21.4(2.1) | 20.7(1.1) |
| Ex.49 | C(50) | d(50) | 20.9(1.6) | 20.1(3.0) |
| Ex.50 | D(50) | d(50) | 18.9(4.0) | 19.0(2.8) |
| Ex.51 | E(50) | d(50) | 21.0(2.2) | 19.9(1.7) |
| Ex.52 | B(50) | e(50) | 21.6(1.7) | 20.0(2.8) |
| Ex.53 | B(50) | f(50) | 20.2(3.2) | 19.4(2.6) |
| Ex.54 | B(50) | g(50) | 20.5(0.9) | 18.6(1.7) |
| Ex.55 | B(50) | h(50) | 19.4(1.9) | 17.3(3.0) |
| Ex.56 | B(50) | i(50) | 20.7(3.0) | 20.9(2.1) |
| Ex.57 | B(50) | j(50) | 21.1(1.3) | 19.8(2.5) |
| Ex.58 | B(50) | k(50) | 20.4(2.3) | 20.2(4.0) |
| Ex.59 | B(50) | l(50) | 19.6(3.0) | 17.8(2.5) |
| Ex.60 | B(50) | m(50) | 20.8(2.6) | 19.9(1.5) |
| Ex.61 | F(50) | d(50) | 22.0(1.9) | 21.0(1.7) |
| Ex.62 | G(50) | d(50) | 21.6(2.1) | 21.1(1.4) |
| Ex.63 | H(50) | n(50) | 22.6(2.8) | 21.3(1.9) |
| Ex.64 | H(50) | o(50) | 22.0(1.1) | 20.9(2.8) |
| Ex.65 | H(50) | p(50) | 22.3(1.5) | 21.2(2.6) |
| Ex.66 | I(50) | n(50) | 22.8(1.0) | 21.4(0.8) |
| Comp.Ex.7 | J(50) | d(50) | 0 | 0 |
| Comp.Ex.8 | B(50) | q(50) | 4.4(0.9) | 7.2(1.3) |
| Comp.Ex.9 | B(50) | r(50) | 0 | 0 |
| Comp.Ex.10 | K(50) | n(50) | 0 | 0 |
| Comp.Ex.11 | H(50) | s(50) | 9.2(1.2) | 4.3(1.1) |
| Comp.Ex.12 | H(50) | t(50) | 2.6(2.0) | 11.8(3.8) |
| Comp.Ex.13 | L(50) | u(50) | 0 | 0 |

Examples 42 to 66

The adhering test was conducted in the same manner as in Example 41 but by preparing the bonding agents of the compositions shown in Table 8 by using the first liquids of the compositions shown in Table 6 and the second liquids of the compositions shown in Table 7. The results were as shown in Table 8 in which numerals in parentheses in the columns of the "First liquid composition" and the "Second liquid composition" represent parts by weight of the liquids.

Examples 41 to 66 were the cases of when the composite resin of the photo-curable type was used, all exhibiting a large adhering strength to the enamel and to the dentin. It is therefore obvious that when the bonding agent of the present invention is used as the adhesive to the composite resin and to the tooth tissue, there is required neither the pretreatment nor the irradiation with light.

Example 41 was the case of when there was used the phosphoric acid group (phosphinico group or phosphono group)-containing polymerizable monomer only as the acidic group-containing monomer. The adhering strength was more improved than in Example 41 when the above acidic group-containing polymerizable monomer was used in combination with the carboxyl group-containing polymerizable monomer (Example 45), when there were further added the multi-valent metal ion-eluting filler and/or water (Examples 42 to 44), and when both of them were effected (Examples 46 to 48).

Examples 61 and 62 were the cases where there was added an agent for promoting the decomposition of the organic peroxide, exhibiting further improved adhering strengths.

Examples 63 to 66 were the cases where the photo sensitized dye and the photo acid generator were added to obtain compositions of the dual curing-type, exhibiting further improved adhering strengths due to the irradiation with light at the time of curing the composite resin.

Comparative Examples 7 to 13

The adhering test was conducted in the same manner as in Example 41 but by preparing the bonding agents of the compositions shown in Table 8 by using the first liquids of the compositions shown in Table 6 and the second liquids of the compositions shown in Table 7. The results were as shown in Table 8.

In Comparative Examples 7 to 12, at least one component essential to the present invention was lacking compared to the Examples and in all cases, the adhering strength has greatly decreased relative to the enamel and to the dentin. Comparative Example 13 was the case of when there was used the organic peroxide/tertiary amine catalyst for polymerization. The composition adhered to neither the enamel nor the dentin.

Example 67

There were separately prepared a first liquid composition A comprising 3 g of PM, 1.5 g of D2.6E and 0.5 g of TMPT, and a second liquid composition a comprising 3.2 g of HEMA, 1.4 g of MMA, 0.1 g of percumyl H and 0.3 g of PhBTEOA. Just before the use, the first liquid and the second liquid were mixed at a ratio of 1:1 to prepare a bonding agent. By using this bonding agent, the adhering strength was measured in compliance with the method of using the chemically-curable composite resin. The results were as shown in Table 9. The adhering strength was 11.4 (1.5) MPa to the enamel and was 11.0 (1.7) MPa to the dentin [numerals in parentheses are standard deviations].

TABLE 9

| | Bonding agent composition | | | |
|---|---|---|---|---|
| | First liquid composition | Second liquid composition | Adhering strength/MPa(S.D.) | |
| | | | Enamel | Dentin |
| Ex.67 | A(50) | a(50) | 11.4(1.5) | 11.0(1.7) |
| Ex.68 | A(50) | b(50) | 11.9(2.1) | 13.7(4.0) |
| Ex.69 | A(50) | c(50) | 13.7(1.4) | 13.3(1.0) |
| Ex.70 | A(50) | d(50) | 14.8(1.2) | 14.9(0.9) |
| Ex.71 | B(50) | a(50) | 12.0(1.6) | 10.7(2.2) |
| Ex.72 | B(50) | b(50) | 12.0(2.0) | 14.0(0.8) |
| Ex.73 | B(50) | c(50) | 14.6(0.9) | 14.1(1.9) |

TABLE 9-continued

| | Bonding agent composition | | | |
|---|---|---|---|---|
| | First liquid composition | Second liquid composition | Adhering strength/MPa(S.D.) | |
| | | | Enamel | Dentin |
| Ex.74 | B(50) | d(50) | 18.2(2.3) | 17.9(3.2) |
| Ex.75 | C(50) | d(50) | 17.0(2.6) | 17.1(1.4) |
| Ex.76 | D(50) | d(50) | 17.8(1.7) | 17.7(0.7) |
| Ex.77 | E(50) | d(50) | 16.5(3.0) | 15.8(2.1) |
| Ex.78 | B(50) | e(50) | 18.1(1.6) | 16.8(3.3) |
| Ex.79 | B(50) | f(50) | 18.8(2.5) | 18.1(1.0) |
| Ex.80 | B(50) | g(50) | 17.0(1.1) | 17.3(1.6) |
| Ex.81 | B(50) | h(50) | 17.4(3.8) | 16.0(1.9) |
| Ex.82 | B(50) | i(50) | 19.2(2.1) | 17.1(3.0) |
| Ex.83 | B(50) | j(50) | 18.2(4.5) | 16.2(1.8) |
| Ex.84 | B(50) | k(50) | 16.9(3.8) | 17.4(2.6) |
| Ex.85 | B(50) | l(50) | 17.2(2.7) | 15.9(2.8) |
| Ex.86 | B(50) | m(50) | 17.2(3.1) | 17.1(2.0) |
| Ex.87 | F(50) | d(50) | 20.8(2.2) | 18.3(2.3) |
| Ex.88 | G(50) | d(50) | 19.3(1.4) | 18.2(3.0) |
| Comp.Ex.14 | J(50) | d(50) | 0 | 0 |
| Comp.Ex.15 | B(50) | q(50) | 4.8(0.6) | 8.5(2.0) |
| Comp.Ex.16 | B(50) | r(50) | 0 | 0 |
| Comp.EX.17 | L(50) | u(50) | 0 | 0 |

Examples 68 to 88

The adhering test was conducted in the same manner as in Example 67 but by preparing the bonding agents of the compositions shown in Table 9 by using the first liquids of the compositions shown in Table 6 and the second liquids of the compositions shown in Table 7. The results were as shown in Table 9.

Examples 67 to 88 were the cases where there were used chemically-curable composite resins of the same adhesive material compositions as those of Examples 41 to 62, all exhibiting large adhering strengths to the enamel and to the dentin. It is therefore obvious that even when the bonding agent of the present invention is used as an adhesive for the chemically-curable composite resin, there is required no pretreatment and the irradiation with light may be omitted.

Comparative Examples 14 to 17

The adhering test was conducted in the same manner as in Example 67 but by preparing the bonding agents of the compositions shown in Table 9 by using the first liquids shown in Table 6 and the second liquids shown in Table 7. The results were as shown in Table 9.

In Comparative Examples 14 to 16, at least one component essential to the present invention was lacking compared to the Examples and in all cases, the adhering strength has greatly decreased relative to the enamel and to the dentin. Comparative Example 17 was the case of when there was used the organic peroxide/tertiary amine catalyst for polymerization. The composition adhered to neither the enamel nor the dentin.

(8) Measurement of Adhering Strengths of Adhesives for Indirectly Restoring the Teeth (Dental Cement) of the Invention.

The tooth surface pretreatment materials used for the adhering test possessed compositions as described below, and were mixed and stirred together just before being used (numerals in parentheses represent parts by weight).

| Tooth surface pretreatment material a: | |
|---|---|
| Liquid A: | PM (15) |
| | MAC-10 (5) |
| | bis-GMA (5) |
| | isopropyl alcohol (16) |
| Liquid B: | water (38) |
| | isopropyl alcohol (19) |
| | PhBTEOA (2) |
| Tooth surface pretreatment material b: | |
| Liquid A: | PM (15) |
| | MAC-10 (5) |
| | bis-GMA (5) |
| | acetone (10) |
| | isopropyl alcohol (6) |
| Liquid B: | water (38) |
| | acetone (19) |
| | sodium p-toluenesulfinate (2) |

(Testing the Adhesion)

A bovine foretooth was pulled out from the lower jaw within 24 hours after the slaughter, and the enamel or the dentin were ground flat to be in parallel with the lip surface by using a #800 emery paper while pouring water. The compressed air was blown to the surface for about 10 seconds to dry it, and a double-sided tape having a hole of a diameter of 3 mm was secured to the surface to specify the adhering area. Then, the tooth surface treatment material was thinly applied onto the tooth surfaces, left to stand for 20 seconds and, then, the compressed air was blown for about 5 seconds to dry it.

The dental cement of the present invention prepared just before the use was applied to the treated tooth surface and to the tooth surface that has not been treated, and a stainless steel attachment having a diameter of 8 mm was adhered thereto with pressure to prepare a test piece. The test piece was maintained in an atmosphere of a temperature of 37° C. and a humidity of 100% for one hour, and was immersed in water maintained at 37° C. for 24 hours, and was subjected to the tensile testing by using a tensile tester (Autograph AG5000 manufactured by Shimadzu Co.) at a crosshead speed of 1 mm/min. Eight adhesion test pieces were measured per a test, and an average value thereof was regarded to be the adhering strength.

TABLE 10

| Powder composition | Aryl borate compound | | | | | Filler | | | | Decomposition promoter | | Other components | |
|---|---|---|---|---|---|---|---|---|---|---|---|---|---|
| | PhBMa | PhNTEOA | FPhBNa | PhBDMPT | PhBDMEE | PMMA | PEMA | P(MMA-EMA) | FASG | CuAA | FeAA | BAPO | BDTPO |
| A | 3 | — | — | — | — | — | 5 | 95 | — | — | — | — | — |
| B | — | 3 | — | — | — | — | 5 | 95 | — | — | — | — | — |
| C | — | — | 3 | — | — | — | 5 | 95 | — | — | — | — | — |
| D | — | — | — | 3 | — | — | 5 | 95 | — | — | — | — | — |
| E | — | — | — | — | 3 | — | 5 | 95 | — | — | — | — | — |
| F | 3 | — | — | — | — | 5 | 5 | 90 | — | — | — | — | — |
| G | — | 3 | — | — | — | 5 | 5 | 90 | — | — | — | — | — |
| H | — | — | 3 | — | — | 5 | 5 | 90 | — | — | — | — | — |
| I | — | — | — | 3 | — | 5 | 5 | 90 | — | — | — | — | — |
| J | — | — | — | — | 3 | 5 | 5 | 90 | — | — | — | — | — |
| K | — | 3 | — | — | — | 5 | 5 | 90 | — | — | — | — | — |
| L | — | 3 | — | — | — | 5 | 5 | 90 | — | — | — | 2 | — |
| M | — | 3 | — | — | — | 5 | 5 | 90 | — | 0.005 | 0.005 | — | — |
| N | 3 | — | — | — | — | 5 | 5 | 90 | — | — | — | — | 2 |
| O | — | 3 | — | — | — | — | — | — | 100 | — | — | — | — |
| P | — | 3 | — | — | — | — | — | — | 100 | — | — | — | — |
| Q | — | 3 | — | — | — | — | — | — | 100 | — | — | 1 | — |
| R | — | 3 | — | — | — | — | — | — | 100 | 0.005 | — | — | — |
| S | — | 3 | — | — | — | 5 | 5 | 90 | — | — | — | — | 1 |
| T | organic peroxide BPO (1 parts by wt.) | | | | | — | — | — | 100 | — | — | — | — |
| U | organic peroxide BPO (1 parts by wt.) | | | | | — | — | — | — | — | — | — | — |

TABLE 11

| Liquid composition | Polymerizable monomer liquid composition (parts by wt.) | | | | | | | | | | | | | |
|---|---|---|---|---|---|---|---|---|---|---|---|---|---|---|
| | Acidic group-containing polymerizable monomer | | | | Other polymerizable monomers | | | | | (B) Organic peroxide | | | | |
| | | | | | | | | | | Per-cumyl H | Per-hexa H | Per-butyl H | Per-butyl D | Per-hexyl I |
| | PM | MAC-10 | MTS | 4-META | MMA | HEMA | bis-GMA | 3G | MTU-6 | | | | | |
| a | 5 | 5 | — | — | 65 | 20 | 3 | 2 | — | 1 | — | — | — | — |
| b | 10 | 5 | — | — | 65 | 20 | — | — | — | 1 | — | — | — | — |
| c | 10 | 5 | — | — | 65 | 20 | — | — | — | — | 1 | — | — | — |
| d | 10 | 5 | — | — | 65 | 20 | — | — | — | — | — | 1 | — | — |
| e | 10 | 5 | — | — | 65 | 20 | — | — | — | — | — | — | 1 | — |
| f | 10 | 5 | — | — | 65 | 20 | — | — | — | — | — | — | — | 1 |
| g | 10 | — | 5 | — | 65 | 20 | — | — | — | 1 | — | — | — | — |
| h | 10 | — | — | 5 | 65 | 20 | — | — | — | 1 | — | — | — | — |
| i | 15 | 5 | — | — | 60 | 20 | — | — | — | 1 | — | — | — | — |
| j | 10 | 5 | — | — | 64.5 | 20 | — | — | 0.5 | 1 | — | — | — | — |
| k | 10 | 5 | — | — | 64 | 20 | — | — | 1 | 1 | — | — | — | — |
| l | 20 | — | — | — | — | 50 | 18 | 12 | — | 1 | — | — | — | — |
| m | 20 | — | — | — | — | 50 | 18 | 12 | — | — | 1 | — | — | — |
| n | 20 | 10 | — | — | — | 40 | 18 | 12 | — | 1 | — | — | — | — |
| o | 10 | 5 | — | — | 65 | 20 | — | — | — | amine compound DMPT(3 parts by wt.) | | | | |
| p | 20 | 10 | — | — | — | 40 | 18 | 12 | — | amine compound DMPT(3 parts by wt.) | | | | |

Example 89

There were separately prepared a powder composition A comprising 9.5 g of P (MMA-EMA), 0.5 g of PEMA and 0.3 g of PhBTEOA, and a polymerizable monomer liquid composition a comprising 0.5 g of PM, 0.5 g of MAC-10, 6.5 g of MMA, 2 g of HEMA, 0.5 g of bis-GMA and 0.1 g of percumyl H. Just before the use, the polymerizable monomer liquid composition and the powder composition were kneaded at a ratio of 1:1.4 to prepare a dental cement. The adhering strength was measured to the tooth surface which has been treated in advance with the pretreatment material a. The results were as shown in Table 12.

TABLE 12

| | Cement composition (parts by wt.) | | Pretreatment material composition | Adhering strength/Mpa(S.D.) | |
|---|---|---|---|---|---|
| | Filler composition | Liquid composition | | Enamel | Dendin |
| Ex. 89 | A(140) | a(100) | a | 19.6 (3.3) | 17.5 (4.1) |
| Ex. 90 | B(140) | a(100) | a | 20.8 (2.2) | 18.4 (1.7) |
| Ex. 91 | C(140) | a(100) | a | 21.2 (4.2) | 18.7 (2.6) |
| Ex. 92 | D(140) | a(100) | a | 20.9 (3.0) | 17.8 (2.9) |
| Ex. 93 | E(140) | a(100) | a | 22.0 (3.7) | 19.3 (3.4) |
| Ex. 94 | F(140) | a(100) | a | 20.6 (2.8) | 17.6 (2.7) |
| Ex. 95 | G(140) | a(100) | a | 20.0 (0.8) | 19.0 (1.7) |
| Ex. 96 | H(140) | a(100) | a | 19.7 (2.4) | 18.4 (0.8) |
| Ex. 97 | I(140) | a(100) | a | 20.8 (3.9) | 20.4 (1.4) |
| Ex. 98 | J(140) | a(100) | a | 20.5 (0.8) | 19.2 (4.3) |
| Ex. 99 | K(140) | a(100) | a | 19.6 (2.2) | 17.6 (2.1) |
| Ex. 100 | L(140) | a(100) | a | 20.4 (4.2) | 20.0 (1.8) |
| Ex. 101 | G(140) | b(100) | a | 18.9 (3.2) | 18.6 (3.7) |
| Ex. 102 | G(140) | c(100) | a | 20.2 (3.9) | 18.6 (2.5) |
| Ex. 103 | G(140) | d(100) | a | 21.6 (3.9) | 17.3 (3.2) |
| Ex. 104 | G(140) | e(100) | a | 22.0 (4.2) | 18.3 (4.2) |
| Ex. 105 | G(140) | f(100) | a | 20.7 (1.8) | 19.1 (2.2) |
| Ex. 106 | G(140) | g(100) | a | 19.3 (0.8) | 19.5 (1.4) |
| Ex. 107 | G(140) | h(100) | a | 22.1 (3.4) | 17.7 (2.4) |
| Ex. 108 | G(140) | i(100) | a | 18.8 (3.2) | 18.3 (2.8) |
| Ex. 109 | G(140) | j(100) | a | 19.5 (2.9) | 17.4 (3.3) |
| Ex. 110 | G(140) | k(100) | a | 20.7 (3.2) | 17.5 (4.2) |
| Ex. 111 | M(140) | a(100) | a | 21.6 (1.2) | 20.0 (1.3) |
| Ex. 112 | N(140) | a(100) | a | 21.0 (1.9) | 19.8 (4.1) |
| Ex. 113 | O(250) | l(100) | — | 15.2 (3.2) | 14.6 (2.3) |
| Ex. 114 | P(250) | l(100) | — | 16.1 (3.5) | 13.7 (2.9) |
| Ex. 115 | P(250) | m(100) | — | 14.7 (2.8) | 14.2 (1.8) |
| Ex. 116 | P(250) | n(100) | — | 14.7 (0.9) | 13.5 (0.8) |
| Ex. 117 | Q(250) | n(100) | — | 14.9 (3.2) | 14.0 (4.0) |

TABLE 12-continued

|  | Cement composition (parts by wt.) | | Pretreatment | Adhering strength/Mpa(S.D.) | |
|---|---|---|---|---|---|
|  | Filler composition | Liquid composition | material composition | Enamel | Dendin |
| Ex. 118 | R(250) | n(100) | — | 15.5 (2.5) | 14.8 (2.4) |
| Ex. 119 | S(250) | n(100) | — | 15.3 (2.6) | 15.0 (2.8) |
| Comp. Ex. 18 | T(140) | o(100) | a | 12.0 (3.2) | 5.3 (2.3) |
| Comp. Ex. 19 | U(250) | p(100) | — | 6.3 (3.3) | 4.6 (1.3) |

Examples 90 to 112

The adhering test to the tooth surface that has been treated in advance with the tooth surface treatment material a was conducted in the same manner as in Example 89 but by preparing the dental cements of the compositions shown in Table 12 by using the powder compositions shown in Table 10 and the polymerizable monomer liquids of the compositions shown in Table 11. The results were as shown in Table 12.

Examples 90 to 112 all exhibited large adhering strengths to the enamel and to the dentin.

Comparative Example 18

The adhering test to the tooth surface that has been treated in advance with the tooth surface pretreatment material a was conducted in the same manner as in Example 89 but by preparing the dental cements of the compositions shown in Table 12 by using the powder compositions shown in Table 10 and the polymerizable monomer liquids of the compositions shown in Table 11. The results were as shown in Table 12.

Comparative Example 18 was the case where there was used an organic peroxide/tertiary amine catalyst for polymerization, exhibiting very decreased adhering strength to the enamel and to the dentin as compared to Examples.

Examples 113 to 119

The adhering test was conducted by preparing the dental cements of the compositions shown in Table 12 by using the powder compositions shown in Table 10 and the polymerizable monomer liquids of the compositions shown in Table 11, but without pretreating the tooth surfaces. The results were as shown in Table 12.

Examples 113 to 119 were the cases of using the resin-reinforced glass ionomer composition all exhibiting relatively large adhering strengths to the enamel and to the dentin without pretreating the tooth surfaces.

Comparative Example 19

The adhering strength was measured in the same manner as in Examples 113 to 119 but preparing a dental cement of a composition shown in Table 12 by using the powder composition shown in Table 10 and the polymerizable monomer liquid of the composition shown in Table 11. The results were as shown in Table 12.

Comparative Example 19 exhibited a decreased adhering strength to the enamel and to the dentin compared to Examples.

TABLE 13

| Paste composition | Paste ① composition (parts by wt.) | | | | | | | | | | |
|---|---|---|---|---|---|---|---|---|---|---|---|
|  | Aryl borate compound | | | Filler | | | Other polymerizable monomer | | | | |
|  | PhBNa | PhBTEOA | FPhBNa | 3Si-Zr | 0.3Si-Ti | FASG | bis-GMA | 3G | D2.6E | NPG | MTU-6 |
| A | 0.3 | — | — | 50 | 50 | — | 12 | 18 | — | — | — |
| B | — | 0.3 | — | 50 | 50 | — | 12 | 18 | — | — | — |
| C | — | — | 0.3 | 50 | 50 | — | 12 | 18 | — | — | — |
| D | — | 0.3 | — | 50 | 50 | — | — | — | 7.5 | 22.5 | — |
| E | — | 0.3 | — | 50 | 50 | — | 12 | 16 | — | — | 2 |
| F | — | 0.3 | — | 50 | 50 | — | 12 | 18 | — | — | — |
| G | — | 0.3 | — | 50 | 50 | — | 12 | 18 | — | — | — |
| H | — | 0.3 | — | 50 | 50 | — | 12 | 18 | — | — | — |
| I | — | 0.3 | — | 50 | 50 | — | 12 | 18 | — | — | — |
| J | — | 0.3 | — | — | — | 100 | — | — | 12 | 18 | — |
| K | 0.3 | — | — | — | 100 | — | 12 | 18 | — | — | 0.005 |
| L | amine compound DMPT(1) | | | 50 | 50 | — | 12 | 18 | — | — | — |
| M | amine compound DMPT(1) | | | — | — | 100 | — | — | 12 | 18 | — |

TABLE 13-continued

| | Paste composition | Paste ① composition (parts by wt.) | | | |
|---|---|---|---|---|---|
| | | Decomposition promoter | | Other components | |
| | | FEAA | CuAA | BAPO | BDTPO |
| | A | — | — | — | — |
| | B | — | — | — | — |
| | C | — | — | — | — |
| | D | — | — | — | — |
| | E | — | — | — | — |
| | F | — | — | 0.2 | — |
| | G | — | — | — | 0.2 |
| | H | 0.005 | — | — | — |
| | I | — | 0.005 | — | — |
| | J | — | — | — | — |
| | K | — | — | — | — |
| | L | — | — | — | — |
| | M | — | — | — | — |

TABLE 14

| Paste composition | Paste ② composition (parts by wt.) | | | | | | | | | | | |
|---|---|---|---|---|---|---|---|---|---|---|---|---|
| | Organic peroxide | | | | Filler | | Acidic group-containing polymerizable monomer | | Other polymerizable monomers | | | |
| | Percumyl H | Perhexa H | Perbutyl H | BPO | 3Si-Zr | 0.3Si-Ti | PM | MAC-10 | MTS | NPG | D2.6E | 3G |
| a | 3 | — | — | — | 50 | 50 | 10 | 2 | — | 6 | 12 | — |
| b | — | 3 | — | — | 50 | 50 | 10 | 2 | — | 6 | 12 | — |
| c | — | — | 3 | — | 50 | 50 | 10 | 2 | — | 6 | 12 | — |
| d | — | 3 | — | — | 50 | 50 | 10 | — | 2 | 6 | 12 | — |
| e | — | 3 | — | — | 50 | 50 | 10 | 2 | — | — | 12 | 5 |
| f | — | — | — | 3 | 50 | 50 | 12 | 18 | — | 6 | — | — |

Examples 120

A homogeneous paste composition A was obtained by kneading 5 g of 3Si—Zr, 5 g of 0.3Si—Ti, 1.2 g of bis-GMA, 1.8 g of 3G and 0.03 g of PhBNa in an agate mortar. Similarly, a homogeneous paste composition a was obtained by kneading 5 g of 3Si—Zr, 5 g of 0.3Si—Ti, 1 g of PM, 0.2 g of MAC-10, 0.6 g of NPG, 1.2 g of D2.6E and 0.03 g of percumyl H. The above paste compositions A and a were kneaded at a weight ratio of 1:1 just before the use to prepare a dental adhesive composition. The adhering strength to the tooth surface which has been treated in advance with the pretreatment material b was measured. The results were as shown in Table 15.

TABLE 15

| | Cement composition (parts by wt.) | | Pretreatment material composition | Adhering strength/ Mpa (S.D.) | |
|---|---|---|---|---|---|
| | Paste ① composition | Paste ② composition | | Enamel | Dendin |
| Ex. 120 | A(100) | a(100) | b | 21.4 (3.2) | 19.2 (2.5) |
| Ex. 121 | B(100) | a(100) | b | 20.8 (2.1) | 18.4 (2.9) |
| Ex. 122 | C(100) | a(100) | b | 21.2 (3.6) | 16.9 (3.2) |
| Ex. 123 | D(100) | a(100) | b | 22.8 (4.2) | 19.3 (3.2) |
| Ex. 124 | E(100) | a(100) | b | 20.9 (1.6) | 20.0 (4.2) |
| Ex. 125 | F(100) | a(100) | b | 20.6 (3.2) | 19.4 (3.2) |
| Ex. 126 | G(100) | a(100) | b | 21.3 (2.8) | 18.5 (0.5) |
| Ex. 127 | B(100) | b(100) | b | 20.7 (2.7) | 17.6 (2.9) |

TABLE 15-continued

| | Cement composition (parts by wt.) | | Pretreatment material composition | Adhering strength/ Mpa (S.D.) | |
|---|---|---|---|---|---|
| | Paste ① composition | Paste ② composition | | Enamel | Dendin |
| Ex. 128 | B(100) | c(100) | b | 20.9 (2.1) | 18.9 (3.2) |
| Ex. 129 | B(100) | d(100) | b | 22.0 (3.5) | 18.4 (1.7) |
| Ex. 130 | B(100) | e(100) | b | 20.5 (3.8) | 20.7 (3.6) |
| Ex. 131 | H(100) | a(100) | b | 22.2 (1.6) | 20.8 (2.0) |
| Ex. 132 | I(100) | a(100) | b | 22.6 (1.9) | 20.8 (1.8) |
| Ex. 133 | J(100) | a(100) | — | 16.6 (2.0) | 15.5 (1.8) |
| Ex. 134 | J(100) | b(100) | — | 17.2 (2.8) | 14.2 (0.9) |
| Ex. 135 | J(100) | c(100) | — | 16.3 (3.2) | 15.4 (0.5) |
| Ex. 136 | J(100) | d(100) | — | 15.4 (3.2) | 14.9 (0.5) |
| Ex. 137 | J(100) | e(100) | — | 16.3 (3.4) | 15.2 (0.9) |
| Ex. 138 | K(100) | a(100) | — | 17.4 (2.0) | 15.9 (1.7) |
| Comp. Ex. 20 | L(100) | f(100) | b | 11.5 (2.3) | 5.3 (2.4) |
| Comp. Ex. 21 | M(100) | f(100) | — | 5.8 (2.4) | 4.2 (2.8) |

Examples 121 to 132

The adhering test to the tooth surface that has been treated in advance with the tooth surface pretreatment material b was conducted in the same manner as in Example 120 but by preparing the dental cements of the compositions shown in Table 15 by using the pastes ① of the compositions shown in Table 13 and the pastes ② of the compositions shown in Table 14. The results were as shown in Table 15.

Examples 121 to 132 all exhibited large adhering strengths to the enamel and to the dentin.

Comparative Example 20

The adhering test to the tooth surface that has been treated in advance with the tooth surface pretreatment material b was conducted in the same manner as in Example 120 but by preparing the dental cement of the composition shown in Table 15 by using the paste ① of the composition shown in Table 13 and the paste ② of the composition shown in Table 14. The results were as shown in Table 15.

Comparative Example 20 was the case of using an organic peroxide/tertiary amine catalyst for polymerization exhibiting very decreased adhering strengths to the enamel and to the dentin compared to Examples.

Examples 133 to 138

The adhering test was conducted by preparing the dental cements of the compositions shown in Table 15 by using the pastes ① of the compositions shown in Table 13 and the pastes ② of the compositions shown in Table 14 but without pretreating the tooth surfaces. The results were as shown in Table 15.

Examples 133 to 138 were the cases of using resin-reinforced glass ionomer compositions of pastes/pastes exhibiting relatively large adhering strengths to the enamel and to the dentin even without pretreating the tooth surfaces.

Comparative Example 21

The adhering strength was measured in the same manner as in Examples 133 to 138 but by preparing the dental cement of the composition shown in Table 15 by using the paste ① of the composition shown in Table 13 and the paste ② of the composition shown in Table 14. The results were as shown in Table 15.

In Comparative Example 21, the adhering strength to the enamel and to the dentin was inferior to those of Examples.
(9) Measurement of Adhering Strengths Using the Dental Pretreatment Material of the Invention.

The adhering materials A to F used for the adhering test were prepared by being mixed and stirred together to possess the following compositions. Here, numerals in parentheses represent parts by weight. The products placed in the market were used in compliance with the methods instructed by the manufacturers.

Chemically-curable adhesives:
Adhesive A:
  Powdery components;
    PMMA (5)
    (MMA-EMA) (95)
    BPO (1)
  Liquid components;
    MMA (65)
    HEMA (20)
    bis-GMA (6)
    3G (4)
    MAC-10 (5)
    DMPT (3)
Adhesive B:
  Powdery components;
    PMMA (5)
    (MMA-EMA) (95)
    PhBTEOA (3)
  Liquid components;
    MMA (65)
    HEMA (20)
    MAC-10 (5)
    PM (5)
    bis-GMA (3)
    3G (2)
    percumyl H (2)
Adhesive C:
  Cement pastes A and B attached to the Bistite II [manufactured by Tokuyama Co.].
Adhesive D:
  Adhesive cement pastes A and B attache to the Panavia fluoro cement [manufactured by Kuraray Co.]
Photo-curable adhesives:
  Adhesive E: Bonding agent attached to the Tokuso Macbond II [manufactured by Tokuyama Co.]
  Adhesive F: Bonding agent attached to the Clearfil Mega Bond (manufactured by Kuraray Co.).
(Pretreatment Method)

A bovine foretooth was pulled out from the lower jaw within 24 hours after the slaughter, and the enamel or the dentin were ground flat to be in parallel with the lip surface by using a #800 emery paper while pouring water. The compressed air was blown to the surface for about 10 seconds to dry it, and a double-sided tape having a hole of a diameter of 3 mm was secured to the surface to specify the adhering area. The dental composition of the present invention was thinly applied onto this area, left to stand for 20 seconds and, then, the compressed air was blown for about 5 seconds to dry it.
(Adhesion by Using the Chemically-Curable Adhesive)

A chemically-curable adhesive was applied to the tooth surface that has been pretreated according to the method described above, and a stainless steel attachment having a diameter of 8 mm was adhered thereto from the upper side with pressure to prepare a test piece. The test piece was maintained in an atmosphere of a temperature of 37° C. and a humidity of 100% for one hour, and was immersed in water maintained at 37° C. for 24 hours, and was subjected to the tensile testing by using a tensile tester (Autograph AG5000 manufactured by Shimazu Co.) at a crosshead speed of 1 mm/min. Eight adhesion test pieces were measured per a test, and an average value thereof was regarded to be the adhering strength.

(Adhesion by Using the Photo-Curable Adhesive) A photo-curable adhesive was applied to the tooth surface that has been prepared according to the method described above, and was cured by the irradiation with light for 10 seconds by using the Power Light (manufactured by Tokuyama Co.]. Then, a wax of a thickness of 1 mm having a hole of a diameter of 8 mm was stuck to the double-sided tape to be in concentric therewith thereby to form a mimic cavity which was, then, filled with a photo-curable composite resin, Palfique Estelite [manufactured by Tokuyama Co.]. The composite resin was covered with a polypropylene sheet, and was irradiated with light for 30 seconds so as to be cured by polymerization thereby to prepare a test piece. The test piece was immersed in water maintained at 37° C. for 24 hours and was, then, put to the tensile testing by using a tensile tester (Autograph AG5000 manufactured by Shimadzu Co.) under a condition of a crosshead speed of 1 mm/min. Eight adhesion test pieces were measured per a test, and an average value thereof was regarded to be the adhering strength.

TABLE 16

| | Pretreatment material composition (parts by wt.) | | | | | | | | |
|---|---|---|---|---|---|---|---|---|---|
| | Pretreatment material (a) | | | Pretreatment material (b) | | | | | Adhering strength/ Mpa (S.D.) |
| | Acidic group-containing polymerizable | Organic | | Aryl | | Decomposition | | | |
| Ex. No. | monomer | peroxide | Others | borate | Water | promoter | Others | Adhesive | Enamel | Dentin |
| 139 | PM (20) | Percumyl H (1) | — | PhBNa (3) | (76) | — | — | A | 18.6(3.2) | 17.3(2.5) |
| 140 | PM (20) | Percumyl H (1) | — | PhBTEOA (3) | (76) | — | — | A | 18.5(2.4) | 17.4(2.7) |
| 141 | PM (20) | Percumyl H (1) | bis-GMA(5) IPA (15) | PhBTEOA (3) | (40) | — | IPA (16) | A | 21.4(3.5) | 18.3(2.4) |
| 142 | PM (20) | Perhexa H (1) | bis-GMA(5) IPA (15) | PhBTEOA (3) | (40) | — | IPA (16) | A | 20.8(3.2) | 19.4(4.2) |
| 143 | PM (20) | Perbutyl H (1) | bis-GMA(5) IPA (15) | PhBTEOA (3) | (40) | — | IPA (16) | A | 20.5(1.5) | 20.3(3.2) |
| 144 | PM (20) | Perbutyl D (1) | bis-GMA(5) IPA (15) | PhBTEOA (3) | (40) | — | IPA (16) | A | 21.6(3.6) | 19.6(2.9) |
| 145 | PM (20) | Perhexyl I (1) | bis-GMA(5) IPA (15) | PhBTEOA (3) | (40) | — | IPA (16) | A | 21.0(2.8) | 20.3(3.2) |
| 146 | PM (20) | Percumyl H (1) | bis-GMA(5) IPA (15) | FPhBNa (5) | (40) | — | IPA (14) | A | 19.3(3.2) | 21.0(3.8) |
| 147 | PM (20) | Percumyl H (1) | bis-GMA(5) IPA (15) | BFPhBNa (1) | (40) | — | IPA (18) | A | 23.3(2.6) | 18.4(2.5) |
| 148 | PM (20) | Percumyl H (1) | bis-GMA(5) IPA (15) | PhBTEOA (3) | (40) | CuAA (0.005) | IPA (16) | A | 22.1(3.0) | 19.8(1.0) |
| 149 | PM (20) | Percumyl H (1) | bis-GMA(5) IPA (15) | PhBTEOA (3) | (40) | FeAA (0.005) | IPA (16) | A | 21.9(3.1) | 20.4(1.8) |
| 150 | PM (20) | Percumyl H (1) | bis-GMA(5) IPA (15) | PhBTEOA (3) | (40) | — | IPA (16) | B | 20.4(3.0) | 18.7(2.9) |
| 151 | PM (20) | Percumyl H (1) | bis-GMA(5) IPA (15) | PhBTEOA (3) | (40) | CuAA (0.005) | IPA (16) | B | 21.1(2.7) | 19.2(1.6) |
| 152 | PM (20) | Percumyl H (1) | bis-GMA(5) IPA (15) | PhBTEOA (3) | (40) | — | IPA (16) | C | 20.0(3.1) | 18.5(3.1) |
| 153 | PM (20) | Percumyl H (1) | bis-GMA(5) IPA (15) | PhBTEOA (3) | (40) | — | IPA (16) | D | 21.4(3.7) | 19.9(0.9) |
| 154 | PM (15) MAC-10(5) | Percumyl H (1) | bis-GMA(5) IPA (15) | PhBTEOA (3) | (40) | — | IPA (16) | A | 22.8(2.5) | 21.5(4.0) |
| 155 | PM (15) MAC-10(5) | Percumyl H (1) | bis-GMA(5) IPA (15) | PhBTEOA (3) | (40) | — | IPA (16) | B | 22.6(3.6) | 21.3(2.3) |
| 156 | PM (15) MAC-10(5) | Percumyl H (1) | 3G (5) acetone(15) | PhBTEOA (3) | (40) | — | acetone(16) | A | 23.3(2.7) | 20.4(1.4) |
| 157 | PM (15) MAC-10(5) | Percumyl H (1) | 3G (5) acetone(15) | PhBTEOA (3) | (40) | — | acetone(16) | C | 22.4(2.9) | 21.4(3.1) |
| 158 | PM (15) 4-META(5) | Percumyl H (1) | bis-GMA(5) IPA (15) | PhBTEOA (3) | (40) | — | IPA (16) | A | 23.3(3.7) | 19.9(3.4) |
| Comp. Ex. | | | | | | | | | | |
| 22 | PM (15) MAC-10(5) | — | bis-GMA(5) IPA (16) | PhBTEOA (3) | (40) | — | IPA (16) | A | 18.6(3.8) | 2.5(1.8) |
| 23 | — | Percumyl H (1) | bis-GMA(5) IPA (35) | PhBTEOA (3) | (40) | — | IPA (16) | A | 0 | 0 |
| 24 | PM (15) MAC-10(5) | Percumyl H (1) | bis-GMA(5) IPA (15) | — | (40) | — | IPA (19) | A | 15.3(3.2) | 0.8(1.3) |
| 25 | PM (15) MAC-10(5) | Percumyl H (1) | bis-GMA(5) IPA (15) | PhBTEOA (3) | — | — | IPA (56) | A | 0 | 1.5(1.5) |
| 26 | PM (15) MAC-10(5) | Percumyl H (0.001) | bis-GMA(5) IPA (16) | PhBTEOA (3) | (40) | — | IPA (16) | A | 17.3(2.8) | 3.1(0.8) |
| 27 | PM (15) MAC-10(5) | Percumyl H (1) | bis-GMA(5) IPA (15) | PhBTEOA (0.001) | (40) | — | IPA (19) | A | 15.6(2.8) | 3.2(1.4) |

Example 139

A solution A comprising 2 g of PM and 0.1 g of percumyl H and a solution B comprising 0.3 g of PhBNa and 7.6 g of water, were mixed together to prepare a homogeneous solution thereof just before the use. The solution was used as a pretreatment material to treat the surface of the tooth. Then, the adhering operation was conducted by using the chemically-polymerizable adhesive A to measure the adhering strength. The results were as shown in Table 16. The adhering strength was 18.6 (3.2) MPa to the enamel and was 17.3 (2.5) MPa to the dentin [numerals in parentheses are standard deviations].

Examples 140 to 158

The adhering strengths to the dentin and to the enamel were measured by using the chemically polymerizable adhesives like in Example 139 but preparing the pretreatment materials of the compositions shown in Table 16. The results were as shown in Table 16.

In all of the Examples, favorable adhesiveness was accomplished to the enamel and to the dentin owing to the pretreatment materials containing the acidic group-containing polymerizable monomer, organic peroxide, water and aryl borate compound, making it possible to accomplish the object of the present invention.

Comparative Examples 22 to 27

The adhering strengths to the dentin and to the enamel were measured by using the chemically polymerizable adhesives like in Example 139 but preparing the pretreatment materials of the compositions shown in Table 16. The results were as shown in Table 16.

In Comparative Examples 22 to 25, at least one component essential to the present invention was lacking compared to the Examples and in all cases, the adhering strength has greatly decreased relative to the enamel and to the dentin. Comparative Examples 26 and 27 were the cases of when the ratios of the essential components were outside the scope of the invention, and in which the adhering strengths to the dentin and to the enamel were small.

TABLE 17

| | Pretreatment material composition (parts by wt.) | | | | | | | | |
|---|---|---|---|---|---|---|---|---|---|
| | Pretreatment material (a) | | | Pretreatment material (b) | | | | | Adhering strength/ Mpa (S.D.) |
| Ex. No. | Acidic group-containing polymerizable monomer | Organic peroxide | Others | Aryl borate | Water | Decomposition promoter | Others | Adhesive | Enamel | Dentin |
| 159 | PM (20) | Percumyl H (1) | — | PhBNa (3) | (76) | — | — | E | 19.3(2.9) | 19.6(2.2) |
| 160 | PM (20) | Percumyl H (1) | — | PhBTEOA (3) | (76) | — | — | F | 19.8(3.2) | 20.4(2.9) |
| 161 | PM (20) | Percumyl H (1) | bis-GMA(5) IPA (15) | PhBTEOA (3) | (40) | — | IPA (16) | E | 22.8(3.4) | 20.5(3.2) |
| 162 | PM (20) | Perhexa H (1) | bis-GMA(5) IPA (15) | PhBTEOA (3) | (40) | — | IPA (16) | E | 21.5(0.4) | 21.6(2.4) |
| 163 | PM (20) | Perbutyl H (1) | bis-GMA(5) IPA (15) | PhBTEOA (3) | (40) | — | IPA (16) | E | 20.8(3.5) | 22.5(0.9) |
| 164 | PM (20) | Perbutyl D (1) | bis-GMA(5) IPA (15) | PhBTEOA (3) | (40) | — | IPA (16) | E | 21.9(3.1) | 21.3(2.4) |
| 165 | PM (20) | Perhexyl I (1) | bis-GMA(5) IPA (15) | PhBTEOA (3) | (40) | — | IPA (16) | E | 23.8(1.9) | 20.9(3.7) |
| 166 | PM (20) | Percumyl H (1) | bis-GMA(5) IPA (15) | FPhBNa (5) | (40) | — | IPA (14) | E | 22.2(4.0) | 23.7(1.5) |
| 167 | PM (20) | Percumyl H (1) | bis-GMA(5) IPA (15) | PhBDMPT (3) | (40) | — | IPA (16) | A | 22.9(1.6) | 21.5(3.1) |
| 168 | PM (20) | Percumyl H (1) | bis-GMA(5) IPA (15) | PhBTEOA (3) | (40) | — | IPA (16) | A | 22.5(1.9) | 20.8(2.1) |
| 169 | PM (20) | Percumyl H (1) | bis-GMA(5) IPA (15) | PhBTEOA (3) | (40) | CuAA (0.005) | IPA (16) | E | 23.6(3.2) | 22.8(2.4) |
| 170 | PM (20) | Percumyl H (1) | bis-GMA(5) IPA (15) | PhBTEOA (3) | (40) | — | IPA (16) | F | 24.2(3.9) | 22.0(2.0) |
| 171 | PM (15) MAC-10(5) | Percumyl H (1) | bis-GMA(5) IPA (15) | PhBTEOA (3) | (40) | — | IPA (16) | E | 22.0(1.9) | 24.7(2.1) |
| 172 | PM (15) MAC-10(5) | Percumyl H (1) | bis-GMA(5) IPA (15) | PhBTEOA (3) | (40) | — | IPA (16) | F | 25.1(1.9) | 24.7(2.4) |
| 173 | PM (15) MAC-10(5) | Percumyl H (1) | 3G (5) acetone(15) | PhBTEOA (3) | (40) | — | acetone(16) | E | 24.7(3.7) | 23.6(1.7) |
| 174 | PM (15) MAC-10(5) | Percumyl H (1) | 3G (5) acetone(15) | PhBTEOA (3) | (40) | — | acetone(16) | F | 25.1(1.0) | 24.7(3.4) |
| 175 | PM (15) 4-META(5) | Percumyl H (1) | bis-GMA(5) IPA (15) | PhBTEOA (3) | (40) | — | IPA (16) | E | 25.7(3.1) | 24.0(3.0) |
| Comp. Ex. | | | | | | | | | | |
| 28 | PM (15) MAC-10(5) | — | bis-GMA(5) IPA (16) | PhBTEOA (3) | (40) | — | IPA (16) | E | 19.3(3.8) | 16.3(2.8) |
| 29 | — | Percumyl H (1) | bis-GMA(5) IPA (35) | PhBTEOA (3) | (40) | — | IPA (16) | E | 0 | 0 |
| 30 | PM (15) MAC-10(5) | Percumyl H (1) | bis-GMA(5) IPA (15) | — | (40) | — | IPA (19) | E | 13.5(3.8) | 12.0(2.8) |
| 31 | PM (15) MAC-10(5) | Percumyl H (1) | bis-GMA(5) IPA (15) | PhBTEOA (3) | — | — | IPA (56) | E | 0 | 5.3(3.2) |

TABLE 17-continued

Pretreatment material composition (parts by wt.)

| | Pretreatment material (a) | | | Pretreatment material (b) | | | | | Adhering strength/ Mpa (S.D.) | |
|---|---|---|---|---|---|---|---|---|---|---|
| Ex. No. | Acidic group-containing polymerizable monomer | Organic peroxide | Others | Aryl borate | Water | Decomposition promoter | Others | Adhesive | Enamel | Dentin |
| 32 | PM (15) MAC-10(5) | Percumyl H (0.001) | bis-GMA(5) IPA (16) | PhBTEOA (3) | (40) | — | IPA (16) | E | 19.3(2.5) | 16.2(2.8) |
| 33 | PM (15) MAC-10(5) | Percumyl H (1) | bis-GMA(5) IPA (15) | PhBTEOA (0.001) | (40) | — | IPA (19) | E | 19.4(2.8) | 13.5(2.9) |

Example 159

A solution A comprising 2 g of PM and 0.1 g of percumyl H and a solution B comprising 0.3 g of PhBNa and 7.6 g of water, were mixed together to prepare a homogeneous solution thereof just before the use. The solution was used as a pretreatment material to treat the surface of the tooth. Then, the adhering operation was conducted by using the adhering material E which was the photo-polymerizable adhesive and by applying the composite resin to measure the adhering strength. The results were as shown in Table 17. The adhering strength was 19.3 (2.9) MPa to the dentin and was 19.6 (2.2) MPa to the enamel [numerals in parentheses are standard deviations].

Examples 160 to 175

The adhering strengths to the dentin and to the enamel were measured by using the photo-polymerizable adhesives like in Example 159 but preparing the pretreatment materials of the compositions shown in Table 2. The results were as shown in Table 17.

In all of the Examples, favorable adhesiveness was accomplished to the enamel and to the dentin owing to the pretreatment materials containing the acidic group-containing polymerizable monomer, organic peroxide, water and aryl borate compound, making it possible to accomplish the object of the present invention.

Comparative Examples 28 to 33

The adhering strengths to the dentin and to the enamel were measured by using the chemically polymerizable adhesives like in Example 159 but preparing the pretreatment materials of the compositions shown in Table 17. The results were as shown in Table 17.

In Comparative Examples 28 to 31, at least one component essential to the present invention was lacking compared to the Examples and in all cases, the adhering strength has greatly decreased relative to the enamel and to the dentin. Comparative Examples 32 and 33 were the cases of when the ratios of the essential components were outside the scope of the invention, and in which the adhering strengths to the dentin and to the enamel were small.

The dental catalyst for chemical polymerization of the present invention exhibits high polymerizing activity even in the presence of oxygen and acidic compound without tinting or discoloring the cured product, is easy to handle and provides a surplus operation time.

The adhesive (bonding agent) for directly restoring the teeth of the present invention makes it possible to adhere the dental restorative as represented by a composite resin to the tooth tissue without pretreatment that was required so far, and makes it possible to accomplish a high adhering strength to both the dentin and to the enamel. Besides, the adhesive can be applied without the need of irradiation with light, exhibiting high degree of adhesiveness not only to the dental restorative of the photo polymerization type but also to the dental restorative of the chemical polymerization type.

The adhesive (dental cement) for indirectly restoring the teeth of the present invention exhibits a large adhering strength to both the dentin and to the enamel compared with the conventional adhesive dental cements.

Besides, the dental restorative of the present invention is highly strong without being tinted or discolored, and makes it possible to accomplish the restoration aesthetically and highly reliably.

Through one time of pretreatment, further, the dental pretreatment material of the present invention enables both the photo-polymerizable adhesive and the chemically polymerizable adhesive to be highly strongly adhered to the enamel and to the dentin compared to when the prior dental pretreatment materials are used.

What is claimed is:

1. A dental catalyst for chemical polymerization comprising:
   an aryl borate compound,
   an acidic compound,
   an organic peroxide, with the organic peroxide containing an amount from 0.1 to 10 mols per mole of the aryl borate, without substantially containing amine compound which exhibits a catalytic action, and
   a metal compound wherein said metal compound promotes the decomposition of the organic peroxide.

2. A dental catalyst for chemical polymerization according to claim 1, wherein an acidic group-containing polymerizable monomer is contained as the acidic compound.

3. A dental catalyst for chemical polymerization according to claim 1, wherein the aryl borate compound has four aryl groups.

4. A dental curable composition containing a polymerizable monomer and the dental catalyst for chemical polymerization of claim 1.

5. A dental curable composition according to claim 4, further containing a photopolymerization initiator.

6. An adhesive for directly restoring the teeth, comprising:
   100 parts by weight of a polymerizable monomer which contains an acidic group-containing polymerizable monomer as an acidic compound, 0.01 to 10 parts by weight of an aryl borate compound, 0.01 to 10 parts by weight of an organic peroxide, with the organic peroxide containing an amount from 0.1 to 10 mols per mole of the aryl borate, 0.0001 to 10 parts by weight of a metal compound wherein said metal compound promotes the decomposition of the organic peroxide, and 1 to 20 parts by weight of a multi-valent metal ion-eluting filler and/or 2 to 30 parts by weight of water, but without substantially containing amine compound as a catalyst.

7. An adhesive for indirectly restoring the teeth comprising:

100 parts by weight of a polymerizable monomer which contains an acidic group-containing polymerizable monomer as an acidic compound, 0.01 to 10 parts by weight of an aryl borate compound, 0.01 to 10 parts by weight of an organic peroxide, with the organic peroxide containing an amount from 0.1 to 10 mols per mole of the aryl borate, 0.0001 to 10 parts by weight of a metal compound wherein said metal compound promotes the decomposition of the organic peroxide, and 50 to 900 parts by weight of a filler, but without substantially containing amine compound as a catalyst.

8. A dental restorative comprising 100 parts by weight of a polymerizable monomer, a catalytic amount of a dental catalyst for chemical polymerization of claim 1 and 50 to 900 parts by weight of a filler.

9. A dental pretreatment material comprising an acidic group-containing polymerizable monomer as an acidic compound, an aryl borate compound, an organic peroxide, with the organic peroxide containing an amount from 0.1 to 10 mols per mole of the aryl borate, a metal compound wherein said metal compound promotes the decomposition of the organic peroxide, and water, but without substantially containing amine compound as a catalyst.

* * * * *